(12) United States Patent
Yun et al.

(10) Patent No.: US 9,836,663 B2
(45) Date of Patent: Dec. 5, 2017

(54) USER AUTHENTICATING METHOD AND HEAD MOUNTED DEVICE SUPPORTING THE SAME

(71) Applicant: Samsung Electronics Co., Ltd., Suwon-si (KR)

(72) Inventors: In-kuk Yun, Suwon-si (KR); Je-in Yu, Seoul (KR); Byeong-hoon Kwak, Uiwang-si (KR); Hyun-jung Kim, Suwon-si (KR); In-hak Na, Yongin-si (KR); Bo-seok Moon, Gunpo-si (KR); Jae-hyun Park, Seoul (KR); Young-eun Lee, Seoul (KR); Ji-yeon Han, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 15/014,652

(22) Filed: Feb. 3, 2016

(65) Prior Publication Data

US 2016/0259986 A1 Sep. 8, 2016

(30) Foreign Application Priority Data

Mar. 5, 2015 (KR) .................. 10-2015-0031245
May 12, 2015 (KR) .................. 10-2015-0066244

(51) Int. Cl.
*G06K 9/00* (2006.01)
*G02B 27/01* (2006.01)
(Continued)

(52) U.S. Cl.
CPC ...... *G06K 9/00892* (2013.01); *A61B 5/04525* (2013.01); *A61B 5/6803* (2013.01); *G02B 27/017* (2013.01); *G02B 27/0172* (2013.01);

*G06F 21/32* (2013.01); *G06K 9/0061* (2013.01); *G06K 9/00617* (2013.01); *G02B 2027/014* (2013.01); *G02B 2027/0138* (2013.01); *G02B 2027/0141* (2013.01);
(Continued)

(58) Field of Classification Search
CPC ..... G06F 21/32; G06F 21/31; G06K 9/00604; G06K 9/0061; G06K 9/00892; G06K 9/00617; G02B 27/017; G02B 27/0172; G06T 5/50
USPC ........................................................ 382/117
See application file for complete search history.

(56) References Cited

U.S. PATENT DOCUMENTS 7,155,035 B2 * 12/2006 Kondo ............... G07C 9/00158
340/5.52
8,009,876 B2    8/2011 Kim et al.
(Continued)

FOREIGN PATENT DOCUMENTS

KR       10-0629550       9/2006
KR    10-2013-0028570     3/2013
(Continued)

*Primary Examiner* — Daniel Mariam
(74) *Attorney, Agent, or Firm* — McAndrews, Held & Malloy, Ltd.

(57) ABSTRACT

A head mounted device (HMD) includes an imaging unit configured to capture at least one image of a partial region of an iris, an electrocardiogram (ECG) sensor configured to receive an ECG signal, and a control unit configured to acquire at least one image of the partial region of the iris and ECG signals, and authenticate a user by using the acquired image(s) of the partial region of the iris and the ECG signals.

19 Claims, 25 Drawing Sheets

(51) Int. Cl.
*G06F 21/32* (2013.01)
*A61B 5/0452* (2006.01)
*A61B 5/00* (2006.01)

(52) U.S. Cl.
CPC ............... *G02B 2027/0178* (2013.01); *G02B 2027/0187* (2013.01); *G06K 2009/00939* (2013.01)

(56) References Cited

U.S. PATENT DOCUMENTS

| | | | | |
|---|---|---|---|---|
| 8,922,342 | B1* | 12/2014 | Ashenfelter | G07C 9/00087 340/5.52 |
| 9,189,686 | B2* | 11/2015 | Bahjat | G06K 9/0061 |
| 9,198,585 | B2 | 12/2015 | Lim et al. | |
| 2007/0047772 | A1* | 3/2007 | Matey | G06K 9/6255 382/117 |
| 2014/0337634 | A1* | 11/2014 | Starner | H04L 9/3231 713/186 |
| 2015/0156196 | A1 | 6/2015 | Kim et al. | |
| 2015/0326570 | A1* | 11/2015 | Publicover | H04N 5/23229 726/4 |

FOREIGN PATENT DOCUMENTS

| | | |
|---|---|---|
| KR | 10-2014-0017734 | 2/2014 |
| WO | 2014-021602 | 2/2014 |

\* cited by examiner

| PARTIAL IMAGE OF IRIS | AVAILABILITY FOR GENERATION OF NORMALIZED IMAGE |
|---|---|
| (a) IMAGE INCLUDING ONLY OUTER CONTOUR LINE | – IRIS SIZE CAN BE ESTIMATED<br>– IMAGE IS NOT AVAILABLE FOR GENERATION OF NORMALIZED IMAGE |
| (b) IMAGE INCLUDING ONLY INNER CONTOUR LINE | – IMAGE IS AVAILABLE FOR GENERATION OF NORMALIZED IMAGE ONLY WHEN IRIS SIZE INFORMATION IS PRESENT |
| (c) IMAGE INCLUDING INNER CONTOUR LINE AND OUTER CONTOUR LINE | – IRIS SIZE CAN BE ESTIMATED<br>– IMAGE IS AVAILABLE FOR GENERATION OF NORMALIZED IMAGE |
| (d) IMAGE INCLUDING NO BOUNDARY LINE | – IRIS SIZE CANNOT BE ESTIMATED<br>– IMAGE IS NOT AVAILABLE FOR GENERATION OF NORMALIZED IMAGE |

FIG. 11

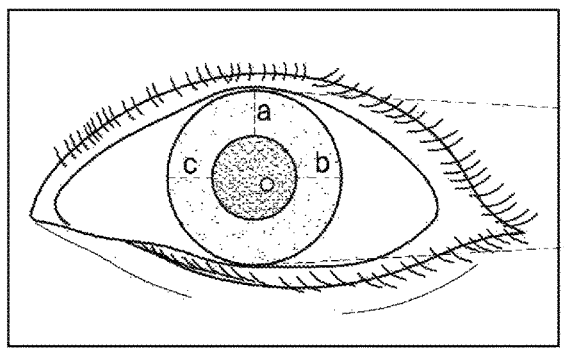

FIG. 12A

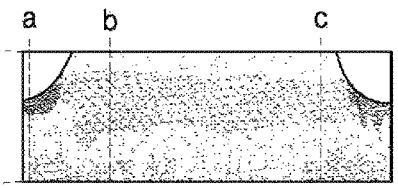

FIG. 12B

| LEFT<br>RIGHT | TEMPLE MIDDLE PORTION | NOSE PAD | TEMPLE PROXIMAL END PORTION |
|---|---|---|---|
| TEMPLE MIDDLE PORTION | 3 | 4 | 2 |
| NOSE PAD | 4 | 5 | 2 |
| TEMPLE PROXIMAL END PORTION | 2 | 2 | 1 |

USER AUTHENTICATING METHOD AND HEAD MOUNTED DEVICE SUPPORTING THE SAME

RELATED APPLICATION(S)

This application claims the benefit of Korean Patent Application No. 10-2015-0031245, filed on Mar. 5, 2015, and Korean Patent Application No. 10-2015-0066244, filed on May 12, 2015 in the Korean Intellectual Property Office, the disclosures of which are incorporated herein in their entirety by reference.

BACKGROUND

The present disclosure relates to user authenticating methods, and more particularly, to user authenticating methods using biometrics and head mounted devices supporting the same.

Much research has been conducted into wearable devices, and various wearable devices have been introduced to the public. Smart watches, head mounted devices (HMDs), and s smart belts are some examples of wearable devices. An HMD is a wearable display device that is worn like glasses and displays an image. The HMD is also referred to as smart glasses.

With the advances in information and communication technologies, various security systems have been required. For example, some security systems use biometric information as a user's unique identification information. In such a security system, an electrocardiogram (ECG), an iris, a fingerprint, a pulse, or the like is used as the biometric information to authenticate a user.

In the case of the iris, iris patterns are different for each individual. Even twins have quite different iris patterns. Iris patterns are forever—they do not change. For these reasons, security technologies using iris information have been in the spotlight.

As another example, the ECG is a record of an action current measured through external electrodes according to contraction and relaxation of a heart muscle. An action potential, which is generated when the heart muscle contracts or relaxes, causes a current to disperse from a heart to a whole body. This current generates a potential difference according to a position of a body. The generated potential difference may be detected and recorded through surface electrodes attached to a skin of the body. Different individuals have different ECG waveforms. Much research has been conducted into security technologies based on ECG waveforms.

SUMMARY

Provided are user authenticating methods using biometric information and HMDs supporting the same.

Additional aspects will be set forth in part in the description which follows and, in part, will be apparent from the description, or may be learned by practice of the presented exemplary embodiments.

According to an aspect of an exemplary embodiment, an HMD includes an imaging unit configured to capture a partial region image of an iris, an electrocardiogram (ECG) sensor configured to receive ECG signals, and a control unit configured to authenticate a user by acquiring at least one of the partial region image, which is captured by the imaging unit, and the ECG signals, which are received through a plurality of electrodes.

The control unit may set an authentication level to each application.

The HMD may further include an input unit configured to receive a user input to execute the application, where when the user input is received from the input unit, the control unit authenticates the user by using one or both of the partial region image(s) and the ECG signals, which is set according to the authentication level.

When either of the partial region image and the ECG signals is not acquired, the control unit is configured to control at least one of the imaging unit and the ECG sensor so as to acquire an appropriate one of the partial region image and the ECG signals.

According to an aspect of another exemplary embodiment, an HMD includes an imaging unit configured to acquire one or more partial images of an iris of a user, and a control unit configured to generate a normalized image for user authentication by combining the one or more partial images.

The control unit may generate the normalized image by using at least one of an outer contour line of the iris and an inner contour line of the iris, which may be included in the partial images.

The control unit may determine positions to be occupied in the normalized image by the partial images and combine the partial images based on the determined positions.

The imaging unit may capture an image of the iris of the user two or more times to generate the normalized image.

The control unit may capture an image of the iris two or more times at preset periods.

When an event occurs, the control unit may authenticate the user by using the generated normalized image. The control unit may control the imaging unit to capture partial region images of the iris two or more times before the occurrence of the event.

The control unit may authenticate the user by comparing a stored image of the entire iris of the user with the generated normalized image.

The control unit may generate the normalized image by using a curvature of an outer contour line of the iris, which is included in the partial image.

When the partial image includes an inner contour line of the iris, the control unit may estimate a size of a pupil from a radius of a virtual circle including the inner contour line by using a curvature of the inner contour line.

When the partial image includes an outer contour line of the iris, the control unit estimates a size of the iris from a radius of a virtual circle including the outer contour line by using a curvature of the outer contour line.

When capturing distances of the acquired partial images are different from one another, the control unit may adjust the size of the acquired partial images based on the capturing distances.

The control unit may perform correction processing on the acquired partial images, the correction processing including at least one of gamma correction, contrast correction, and sharpness correction.

When a predetermined event requiring user authentication occurs, the display unit may provide a user interface for capturing an image of the iris of the user, and a user interface for guiding a position to be viewed by a user's eye so as to acquire partial images of the iris, including a specific position in an entire region of the iris.

According to an aspect of another exemplary embodiment, an HMD includes a plurality of electrodes configured to detect ECG signals disposed in the HMD, and a control unit configured to receive ECG signals through the plurality of electrodes and perform user authentication based on the received ECG signals.

The plurality of electrodes may be disposed in at least one of a first contact portion that is disposed on an inner side of the HMD and contacts a user's head when the user wears the HMD, and a second contact portion that is contactable with other body parts except for the head.

The HMD may include a temple, a lens frame, and a nose pad. The first contact portion may include at least one of a middle portion of the temple and the nose pad, which contact the user when the user wears the HMD.

The second contact portion may include at least one an upper side of the lens frame, a proximal end portion of the temple connected to the lens frame, and a distal end portion of the temple.

When a plurality of ECG signals are received from the plurality of electrodes disposed in the HMD, the control unit determines at least one of the plurality of ECG signals for the user authentication according to a setting, and performs the user authentication based on the determined at least one ECG signal.

The control unit may determine whether the HMD is worn by the user.

The HMD may further include a display unit. When it is determined that the HMD is not worn by the user, the control unit may control the display unit to output guidance for wearing the HMD.

The control unit may receive a user input to authenticate the user through at least one biometric sensor other than an ECG sensor, receive biometric information of the user through the at least one biometric sensor, determine a first matching rate between the received biometric information of the user and preregistered biometric information corresponding to the biometric information, determine a second matching rate between the ECG signals received through the plurality of electrodes and the preregistered ECG signal, and perform the user authentication by combining the first matching rate and the second matching rate.

In order to determine the second matching rate, a weight value may be set to at least a part of a waveform of the received ECG signal.

The HMD may further include an input unit configured to receive a user input to execute an application, and the control unit may confirm electrodes set for authentication of the application, for which the user input is received through the input unit, among the plurality of electrodes, and receive ECG signals through the confirmed electrodes.

The HMD may further include a display unit, and the control unit may be configured to determine a third matching rate between the ECG signals received through the plurality of electrodes and a preregistered ECG signal, compare the third matching rate with at least one fourth matching rate determined based on at least one ECG signal received for a predetermined time before the reception of the ECG signals, and control the display unit to output a message indicating that the user has health problems when the third matching rate is less than the at least one fourth matching rate.

BRIEF DESCRIPTION OF THE DRAWINGS

These and/or other aspects will become apparent and more readily appreciated from the following description of the exemplary embodiments, taken in conjunction with the accompanying drawings in which:

FIGS. 10 and 11 are diagrams for describing an example of partial images of an iris, according to an exemplary embodiment;

FIGS. 12A and 12B are diagrams for describing normalization of an iris image, according to an exemplary embodiment;

DETAILED DESCRIPTION

Figure 1:
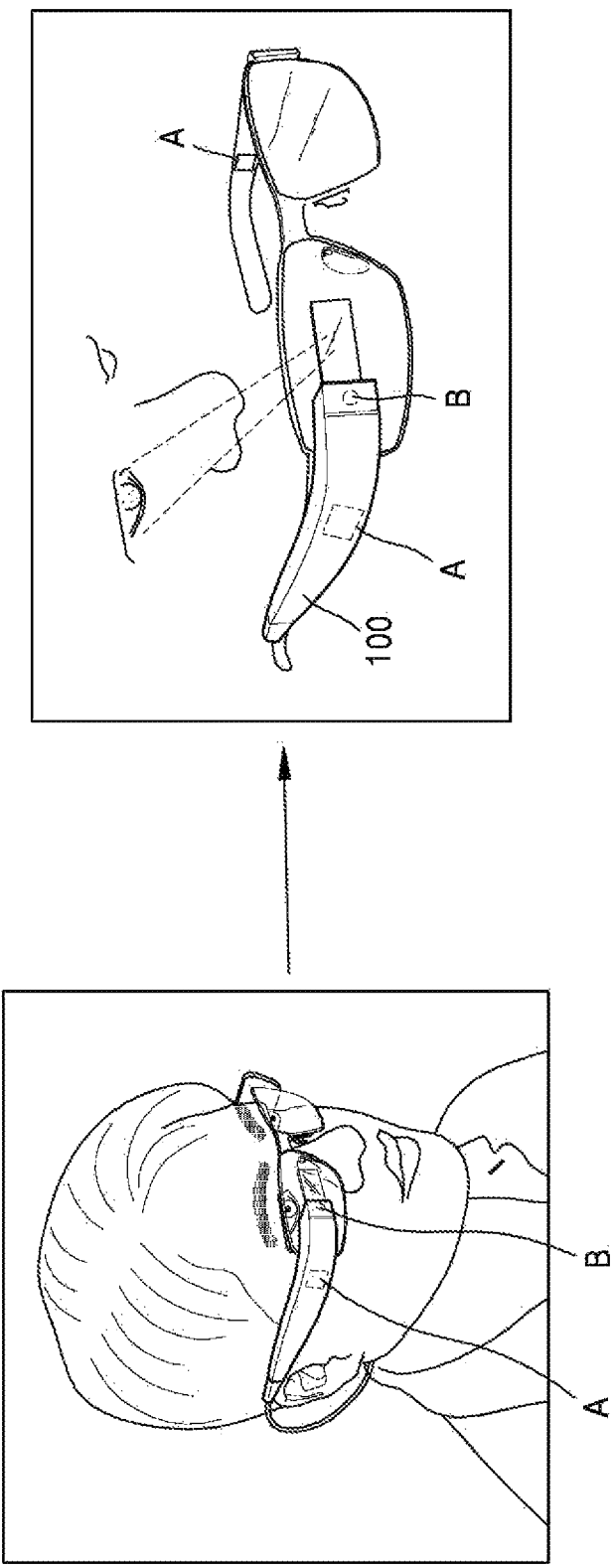
FIG. 1 is a conceptual diagram for describing a user authenticating method using biometric information, according to an exemplary embodiment.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

Hereinafter, exemplary embodiments of the inventive concept will be described in detail with reference to the accompanying drawings. The inventive concept may, however, be embodied in many different forms and should not be construed as being limited to the embodiments set forth herein; rather, these exemplary embodiments are provided so that this disclosure will be thorough and complete, and will fully convey the concept of the inventive concept to those of ordinary skill in the art. As used herein, the term "and/or" includes any and all combinations of one or more of the associated listed items.

It will be understood that, although the terms "first," "second," etc. may be used herein to describe various elements, these elements should not be limited by these terms. These terms are only used to distinguish one element from another element.

The terms used in this specification are general terms currently widely used in the art in consideration of functions in regard to the inventive concept, but the terms may vary according to the intention of those of ordinary skill in the art, precedents, or new technology in the art. In addition, specified terms may be selected by the applicant, and in this case, the detailed meaning thereof will be described in the detailed description of the inventive concept. Thus, the terms used in the specification should be understood not as simple names but based on the meaning of the terms and the overall description of the inventive concept.

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises," "comprising," "includes," and/or "including," when used in this specification, specify the presence of stated features, integers, steps, operations, elements, and/or components, but do not preclude the presence or addition of one or more other features, integers, steps, operations, elements, components, and/or groups thereof.

FIG. 1 is a conceptual diagram for describing a user authenticating method using biometric information, according to an exemplary embodiment. As illustrated in FIG. 1, the head mounted device (HMD) 100 may acquire biometric information of a user in a state of being worn by the user.

The HMD 100 may acquire an image of the user's iris as biometric information. For example, the HMD 100 may acquire the iris image through an imaging unit B.

In a case where partial images of a user's iris are captured through the imaging unit B, the HMD 100 may combine the partial images to a combined partial image and use the combined partial image for user authentication.

In a case where a partial image of the iris is captured, a capturing distance from the imaging unit B of the HMD 100 to a user's eye may be a predetermined threshold value or less. In this case, it may be difficult for the imaging unit B to acquire an image of the entire iris. In another example, when a view angle of the imaging unit B of the HMD 100 is narrow, it may be difficult to capture an image of the entire iris. In another example, when an image of a peripheral region of the user's iris is captured together, it may not be possible to capture an image of the entire iris.

In another exemplary embodiment, the HMD 100 may acquire an ECG signal as biometric information through electrodes A disposed at predetermined positions to contact the user's head. The electrodes A are illustrated in FIG. 1 as being disposed at temples of the HMD 100, but are not limited thereto. For example, a plurality of electrodes may be disposed in the HMD 100 as shown in FIG. 2A.

Figure 2A:
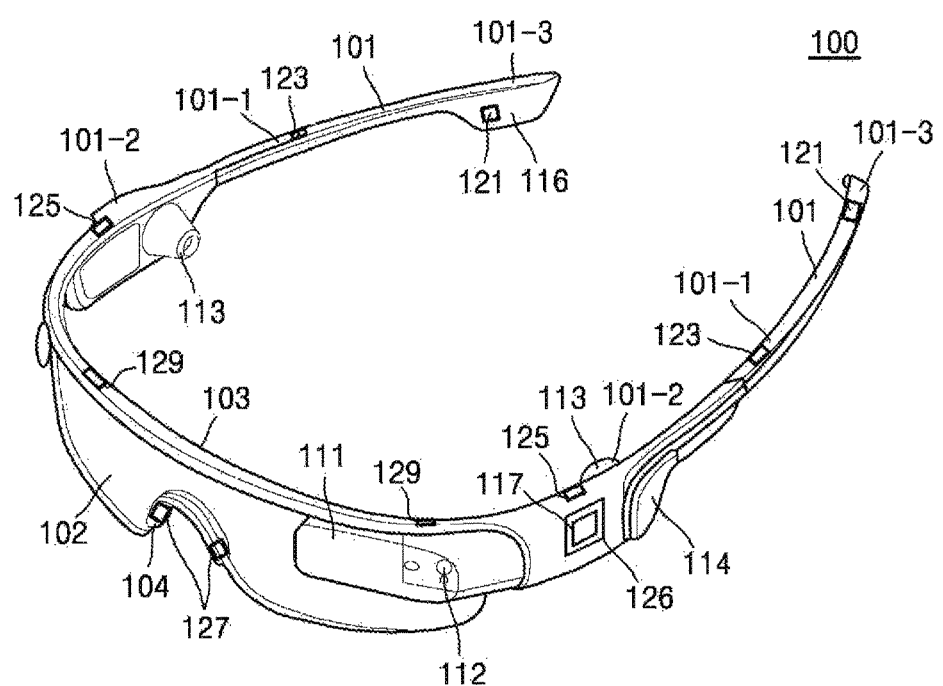
FIG. 2A is a perspective view of an HMD for describing the user authenticating method using biometric information, according to an exemplary embodiment.

FIG. 2A is a perspective view of the HMD 100 for describing the user authenticating method using biometric information, according to an exemplary embodiment.

The HMD 100 may include temples 101, a lens 102, a lens frame 103, a nose pad 104, electrodes 121, 123, 125, 126, 127, and 129, a display unit 111, an imaging unit 112, an audio output unit 113, an input unit 114, and a power supply unit 116. The elements included in the HMD 100 may be attached (or mounted) to the outside of the HMD 100. In another exemplary embodiment, the elements included in the HMD 100 may be embedded in the HMD 100. An embodiment may have the HMD 100 omit one or more of the above-mentioned elements and/or include other elements than those described above. For example, although not illustrated, the HMD 100 may further include a sensing unit, such as an ECG sensor or a fingerprint sensor, so as to sense biometric information of the user. Additionally, the number of a type of an element, for example, electrodes, may vary.

When the user wears the HMD 100, the temples 101 may partially contact the user and fix the HMD 100 to the user. The temples 101 may be made of plastic and/or metal and may include interconnects that mutually connect elements included in the temples 101. In another exemplary embodiment, the temples 101 may include connection members (not illustrated) that make a part of the temples 101 be foldable. In another exemplary embodiment, the temples 101 may be flexible. The temples 101 may be configured to hook over a user's ears, but are not limited thereto. In another exemplary embodiment, the temples 101 may extend to the back of a user's head.

The lens 102 may be made of a transparent material so as to allow the user to see through the lens 102. The lens 102 may be made of, for example, glass, or plastic such as polycarbonate, but is not limited thereto. The lens 102 may include at least one of anti-reflective coating, anti-glare coating, anti-fog coating, and ultraviolet protection coating.

The lens frame 103 may fix or hold the lens 102. The lens frame 103 may be made of plastic and/or metal and may include interconnects that mutually connect elements included in or attached to the lens frame 103. In another exemplary embodiment, the lens frame 103 may include connection members (not illustrated) that make a part of the lens frame 103 be foldable. In another exemplary embodiment, the lens frame 103 may be flexible.

When the user wears the HMD 100, the nose pad 104 may contact the bridge of the user's nose and fix the HMD including the lens 102 to the user.

The lens frame 103 and the nose pad 104 may be integrally formed, but are not limited thereto. The temples 101 and the lens frame 103 may be integrally formed, but are not limited thereto.

The imaging unit 112 may include an image sensor (not illustrated). The imaging unit 112 may support optical zoom or digital zoom by using a plurality of lenses and/or image processing. A recognition range of the imaging unit 112 may be variably set according to an angle of a camera and surrounding environment conditions. When the imaging unit 112 includes a plurality of cameras, the imaging unit 112 may receive a three-dimensional (3D) still image or a 3D motion by using the plurality of cameras.

The imaging unit 112 may include an infrared camera and a time-of-flight (TOF) camera.

The imaging unit 112 may further include an illumination unit. For example, the imaging unit 112 may include at least one of a visible-ray illumination unit configured to acquire light reflected from a subject with respect to a visible-ray light source and an infrared-ray (IR) illumination unit configured to acquire light reflected from a subject with respect to an infrared-ray light source. Either of the visible-ray illumination unit and the infrared-ray illumination unit may be appropriately selected as the illumination unit according to characteristics of the subject and a size of the subject.

The imaging unit 112 is illustrated in FIGS. 2A to 2E as being disposed at one side of the display unit 111 of the HMD 100, but are not limited thereto. For example, the imaging unit 112 may be disposed on the lens 102 or the lens frame 103. Alternatively, the HMD 100 may include a plurality of imaging units 112. For example, at least one imaging unit may be additionally disposed in the HMD 100 so as to capture an image of the user's iris. In this case, the at least one imaging unit may be disposed on an inner side of the lens frame 103 to capture the iris image.

The imaging unit 112 may be integrally formed with the HMD 100 or may be formed separately from the HMD 100. A separate device (not illustrated) including the separate imaging unit 112 may be electrically connected to the HMD 100 through a communication unit or an input/output unit.

The imaging unit 112 may acquire an image of the user's iris. The imaging unit 112 may capture two or more partial images of the iris so that the partial images can be combined under control of a control unit to a combined partial image. Acquisition of further iris images may stop when the ratio of a region corresponding to the combined partial image to the entire iris reaches a preset threshold value or more. The combined partial image that corresponds to the threshold ratio may be enough to be able to analyze the iris image for iris authentication.

The imaging unit 112 may capture the iris image two or more times at preset periods. The imaging unit 112 may previously capture partial images of the iris two or more times prior to occurrence of a predetermined event requiring user authentication.

The plurality of electrodes 121, 123, 125, 126, 127 and 129 may receive ECG signals from the user. The plurality of electrodes 121, 123, 125, 126, 127 and 129 may be disposed at various positions of the HMD 100. For example, the plurality of electrodes 121, 123, 125, 126, 127 and 129 may be disposed in the temples 101, the lens frame 103, and the nose pad 104.

In a case where the electrodes are attached to the temples 101, the electrodes may also be disposed at an outer side, an upper side, and a lower side that may contact a user's hand when the user wears the HMD 100, as well as the inner side contacting the user's head/face. With reference to a length extending from a connection portion of the temple 101 and the lens frame 103 to an end of the temple 101, a "temple proximal end portion 101-2" refers to a portion that is connected to the lens frame 103, a "temple middle portion 101-1" refers to a portion that contacts the user when the user wears the HMD 100, and a "temple distal end portion 101-3" refers to a portion from the temple middle portion to the end of the temple 101.

The temple proximal end portion 101-2 may refer to a portion from the connection portion of the temple 101 and the lens frame 103 to a portion that does not contact the user when the user wears the HMD 100. For example, the temple proximal end portion 101-2 may refer to a portion from the connection portion of the temple 101 and the lens frame 103 to a portion spaced perpendicular to the user's temple. In a case where the HMD 100 is configured such that the user's temple contacts the temple 101, the temple proximal end portion 101-2 may refer to a portion from the connection portion of the temple 101 and the lens frame 103 to a portion spaced perpendicular to an end portion of the user's eye. The electrode(s) 125 and the electrode 126 may be disposed at the temple proximal end portion 101-2 of the HMD 100 and receive an ECG signal from the user by a contact with a user's finger or the like.

When the user wears the HMD 100, the temple middle portion 101-1 may be the temple 101 that contacts the user. For example, when the user wears the HMD 100, the temple middle portion 101-1 may range from a portion that first contacts the user's temple to a portion of the temple 101 that contacts a user's ear over which the temple 101 is hooked (or supported). In a case where the electrode(s) 123 is disposed in the inner side of the temple middle portion 101-1, an ECG signal may be received through the electrode(s) 123 while the user wears the HMD 100 without separate user input.

When the user wears the HMD 100, the temple distal end portion 101-3 may not contact the user and may refer to a portion from the temple middle portion 101-1 to the end of the temple 101. An ECG may be measured more accurately when the spacing between the electrodes is larger. For example, an ECG may be measured more accurately when one electrode is disposed in the temple distal end portion 101-3 and another electrode is disposed in the nose pad 104 that is far away from the temple distal end portion 101-3.

The electrode 126 may be disposed on an outer side of the temple proximal end portion 101-2, the electrode(s) 125 may be disposed on an upper side thereof, and other electrodes (not illustrated) may be disposed in a lower side thereof. In another example, the electrode(s) 123 may be disposed in the inner side of the temple middle portion 101-1. In another example, the electrode 121 may be disposed on an outer side of the temple distal end portion 101-1, and other electrodes may be disposed on an upper side and a lower side of the temple distal end portion 101-1. However, these are only exemplary and the technical spirit of the inventive concept is not limited thereto. At least one of the electrodes 121, 123, 125, 126, 127 and 129 may be disposed to an overlapping configuration with a part that performs a function for the HMD 100. For example, the electrode 126 may be under the power button 117. When the electrode 126 is under the power button 117, the electrode 126 may be larger than the power button 117. In other words, a part of the electrode 126 may be covered by the power button 117, and an outer portion of the electrode 126 may be exposed. The exposed outer portion of the electrode 126 may receive an ECG signal from the user through a contact with the user's finger or the like.

In another exemplary embodiment, at least one of the electrodes 121, 123, 125, 126, 127 and 129 may be disposed adjacent to a part that performs a function for the HMD 100. For example, the electrode 126 may be formed to have a loop (or ring) shape, and the loop-shaped electrode 126 may be disposed to surround the power button 117. In this case, an inner boundary of the electrode 126 may be in contact with an outer boundary of the power button 117.

In a case where the electrode 126 is disposed under the power button 117 or is disposed adjacent to the power button 117, user inputs may be simultaneously received from the user through the electrode 126 and the power button 117. For example, in a case where the electrode 126 is disposed under the power button 117 or is disposed adjacent to the power button 117, the user may simultaneously touch the electrode 126 and the power button 117. In this case, an ECG signal may be received from the user through the electrode 126, and power may be supplied to each element of the HMD 100 by the input of the power button 117.

The power button 117 is described as the configuration that performs the function of the HMD 100, but it is not limited thereto. For example, besides the power button 117, any configuration (e.g., a touch pad) may also be applied as long as the configuration is simultaneously touched with the electrode when touched by the user.

The electrode(s) 129 may be disposed in the lens frame 103. The electrode(s) 129 is illustrated in FIG. 2A as being disposed on an upper side of the lens frame 103, but is not limited thereto. For example, the electrode(s) 129 may be disposed on a lateral side of the lens frame 103. The electrode(s) 129 may be disposed on both ends of the lens frame 103. However, the inventive concept is not limited thereto. There may be, for example, a single electrode 129 that may be disposed in the middle of the lens frame 103. Since the electrode(s) 129 is disposed on the lens frame 103, the user may easily touch the electrode(s) 129 with his or her finger(s) when the user is wearing the HMD 100.

The electrode(s) 127 may be disposed in the nose pad 104. In a case where the electrode(s) 127 are disposed in the nose pad 104, the electrode(s) 127 may contact the user's nose bridge when the user wears the HMD 100. In this case, while the user wears the HMD 100, an ECG signal may be received from the user without separate user input (e.g., touch input). Hereinafter, for convenience of description, it will be assumed that the inner side of the temple middle portion 101-1 and the nose pad 104 are portions that contact the user when the user wears the HMD 100, and may also be referred to as "contact portions". The temple proximal end portion 101-2, the temple distal end portion 101-3, and the lens frame 103 are portions that do not contact the user when the user wears the HMD 100 and may be referred to as "non-contact portions". While the non-contact portions do not touch the face or head when the HMD 100 is worn in a normal manner, they may be touchable by the user's finger or the like.

In addition, the display unit 111, the imaging unit 112, the audio output unit 113, the input unit 114, and the power supply unit 116, which are included in the HMD 100, will be described below with reference to FIG. 4 and subsequent drawings.

Figure 2B:
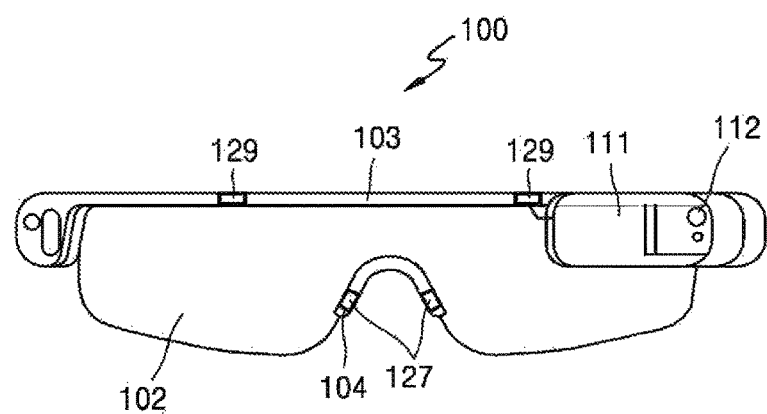
FIG. 2B is a front view of the HMD for describing the user authenticating method using biometric information, according to an exemplary embodiment.

FIG. 2B is a front view of the HMD 100 for describing the user authenticating method using biometric information, according to an exemplary embodiment.

Referring to FIG. 2B, the electrode(s) 129 may be disposed on the upper side of the lens frame 103. However, the inventive concept is not limited thereto. For example, the electrode(s) 129 may be disposed on the display unit 111 or the lens 102. In a case where the electrode(s) 129 is disposed on the lens 102, the electrode 129 may be a transparent electrode. In another example, the electrode(s) 129 may be disposed in a lateral side of the lens frame 103, except for a lower side of the lens frame 103 in which the lens 102 is attached (or mounted).

The electrode(s) 127 may be disposed in the nose pad 104. According to some exemplary embodiments, the nose pad 104 may be omitted. In a case where the electrode(s) 127 is disposed in the nose pad 104, the electrode(s) 127 may contact the user when the user wears the HMD 100. In this manner, while the user wears the HMD 100, an ECG signal may be received through the electrode(s) 127 without separate input by the user (e.g., touch input).

Figure 2C:
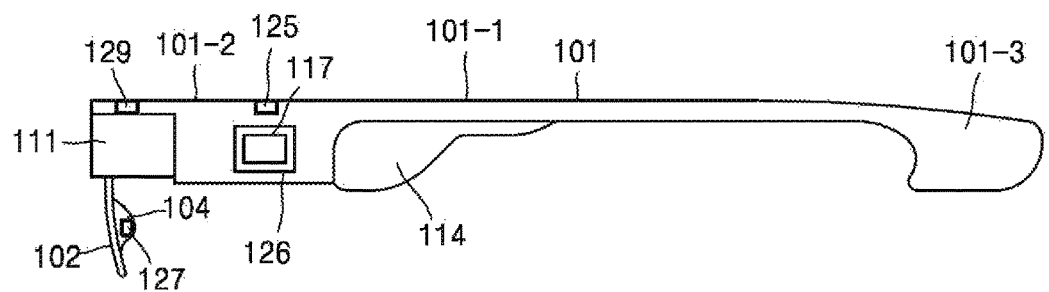
FIG. 2C is a left side view of the HMD for describing the user authenticating method using biometric information, according to an exemplary embodiment.

FIG. 2C is a left side view of the HMD 100 for describing the user authenticating method using biometric information, according to an exemplary embodiment.

Referring to FIG. 2C, the electrodes may be disposed in the lens frame 103, the nose pad 104, and the temple 101. In an exemplary embodiment, the electrode 126 may be disposed to be overlapped by the power button 117.

Figure 2D:
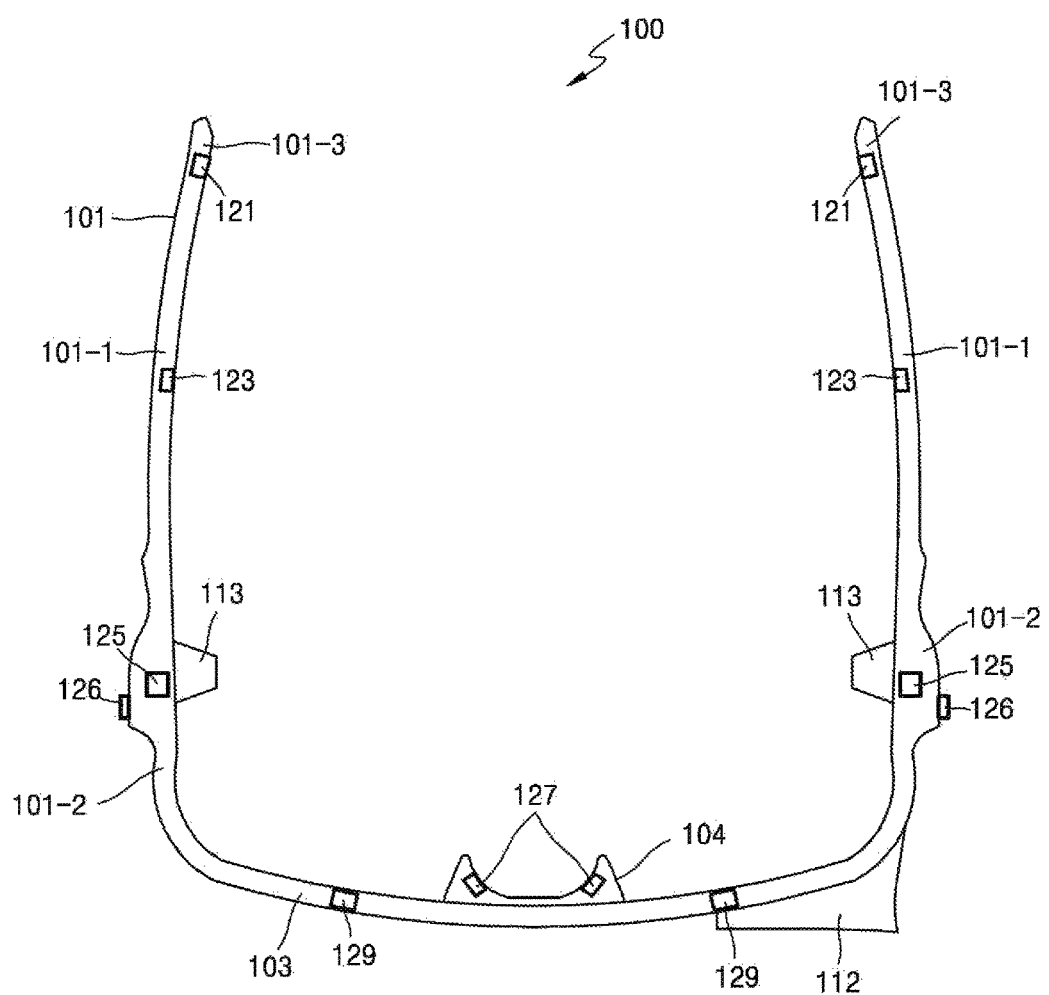
FIG. 2D is a plan view of the HMD for describing the user authenticating method using biometric information, according to an exemplary embodiment.

FIG. 2D is a plan view of the HMD 100 for describing the user authenticating method using biometric information, according to an exemplary embodiment.

Referring to FIG. 2D, electrodes may be disposed in the temple 101, the lens frame 103, and the nose pad 104.

Figure 2E:
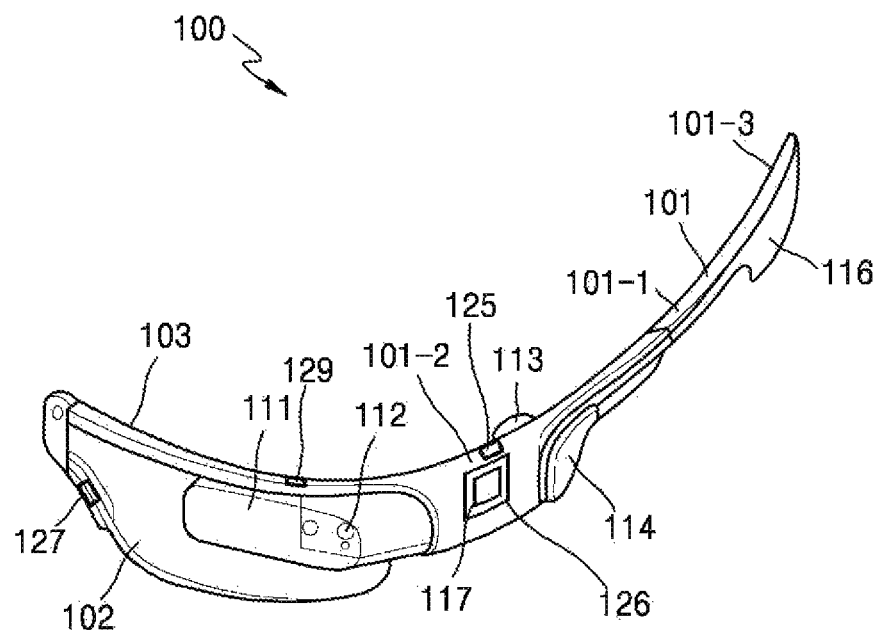
FIG. 2E is a perspective view of an HMD for describing a user authenticating method using biometric information, according to another exemplary embodiment.

FIG. 2E is a perspective view of an HMD 100, for describing a user authenticating method using biometric information, according to another exemplary embodiment.

FIG. 2E illustrates a monocle-like HMD 100 that is fixed to a user's face with a user's left ear and a left side of a nose pad 104. However, the HMD 100 is not limited thereto. For example, the HMD 100 may be fixed to a user's face through a user's right ear and a right side of the nose pad 104.

The HMD 100 of FIG. 2E may be substantially the same as the left side of the HMD 100 of FIG. 2A from the center of the lens frame 103.

Two or more electrodes may be disposed in the temple 101, the lens frame 103, and the nose pad 104.

A more accurate ECG signal may be received when electrodes are disposed at various positions of the HMDs 100 according to various exemplary embodiments. In other words, an ECG may be measured more accurately when the spacing between the electrodes is larger. Therefore, a more accurate ECG signal may be received through electrodes spaced farther apart from one another, according to a user's selection.

In addition, an ECG signal may be received through the electrode(s) contacting the user while the user is wearing the HMD 100 without separate user input, and the user may be authenticated based on the received ECG signal.

Figure 3A:
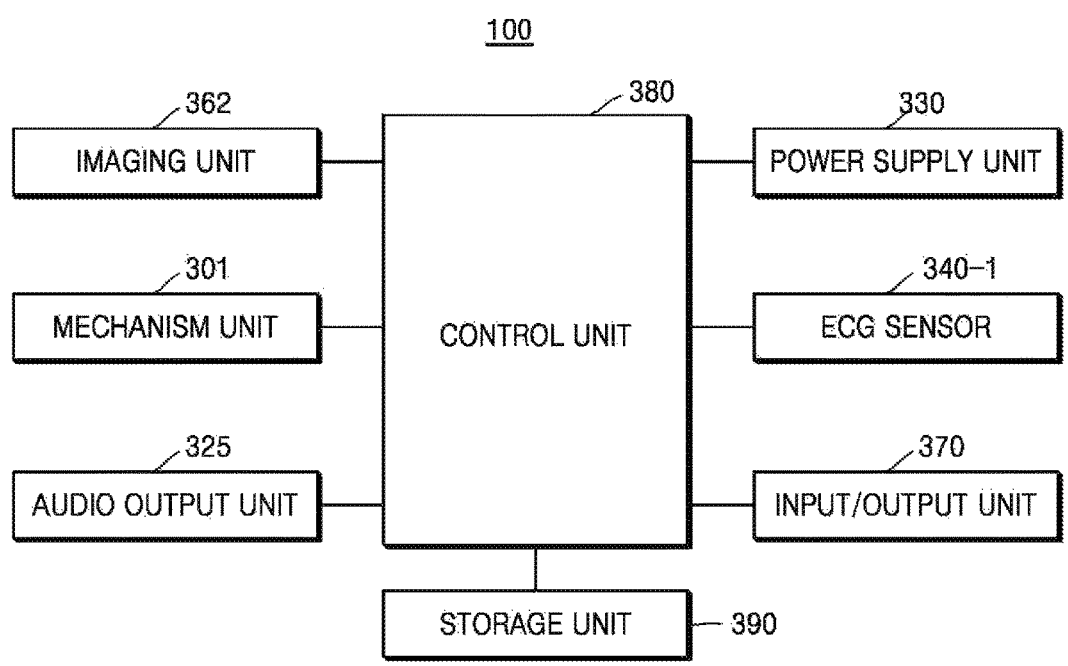
FIGS. 3A and 3B are block diagrams of an HMD for describing a user authenticating method using biometric information, according to an exemplary embodiment.
Figure 3B:
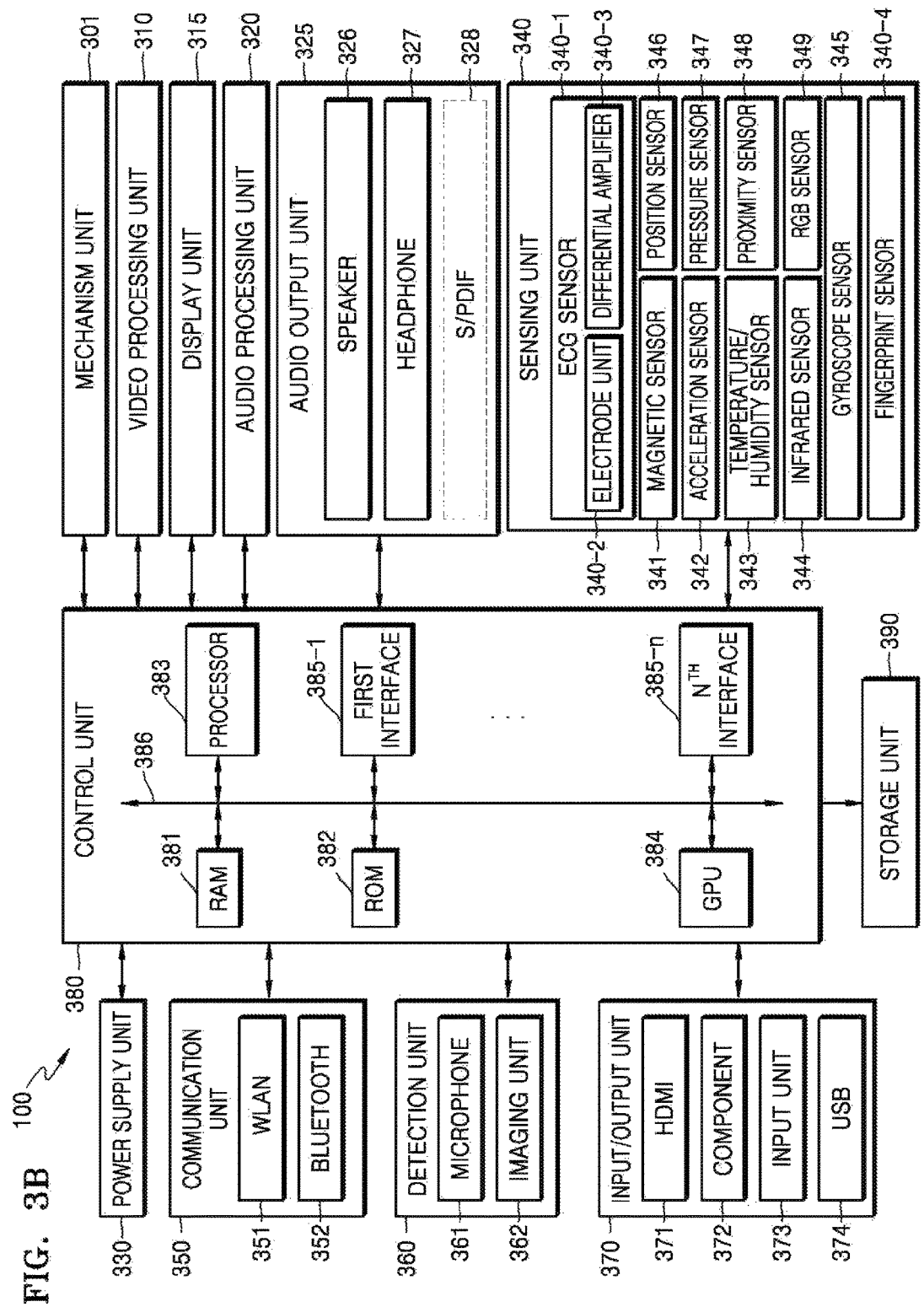

FIGS. 3A and 3B are block diagrams of an HMD 100 according to an exemplary embodiment.

Referring to FIG. 3A, the HMD 100 may include a mechanism unit 301, an audio output unit 325, a power supply unit 330, an ECG sensor 340-1, an imaging unit 362, an input/output unit 370, a control unit 380, and a storage unit 390. The HMD 100 may be implemented with a larger number of elements than those illustrated in FIG. 3A, or may be implemented with a smaller number of elements than those illustrated in FIG. 3A.

For example, as illustrated in FIG. 3B, the HMD 100 may further include a video processing unit 310, a display unit 315, an audio processing unit 320, a sensing unit 340, a communication unit 350, and a detection unit 360.

The mechanism unit 301 may include a temple 101, a lens 102, a lens frame 103, and a nose pad 104. Since the elements included in the mechanism unit 301 are substantially the same as those described with reference to FIGS. 2A to 2E, detailed descriptions thereof will be omitted.

The video processing unit 310 may process video data received by the HMD 100. The video processing unit 310 may perform image processing, such as decoding, scaling, noise filtering, frame rate conversion, and/or resolution conversion, with respect to the video data.

The display unit 315 may display content (e.g., moving image) input through the communication unit 350 or the input/output unit 370. The display unit 315 may output an image stored in the storage unit 390 under control of the control unit 380. In addition, the display unit 315 may display a voice user interface (UI) (including a voice command guide) for performing a voice recognition tasks or a motion UI (including a user motion guide for motion recognition) for performing a motion recognition tasks.

The display unit 315 may include a translucent optical waveguide (e.g., prism). The translucent optical waveguide may focus an image on a fovea of a retina of a user wearing the HMD 100 by reflecting light output from a projector.

The display unit 315 may output various screens based on ECG signals that the HMD 100 receives from a plurality of electrodes under control of the control unit 380. For example, when the control unit 380 determines that the user is not wearing the HMD 100 correctly, the display unit 315 may output a message that requests the user to correctly wear or adjust the HMD 100 for better contact. This may be because the user is wearing the HMD 100 skewed and so the electrodes are not making good contact with the user's face/head.

When a predetermined event requiring user authentication occurs (e.g., a predetermined application is executed), the display unit 315 may display a UI for capturing an iris of a user under control of the control unit 380.

The display unit 315 may display a UI under control of the control unit 380 to guide the user to look at specific positions so as to acquire partial images of the user's iris, including a specific position to get an image of the entire iris if possible.

The audio processing unit 320 may process audio data. The audio processing unit 320 may perform audio processing such as decoding, amplification, and/or noise filtering with respect to the audio data. The audio processing unit 320 may include a plurality of audio processing modules to process audio corresponding to a plurality of content.

The audio output unit 325 may output audio (e.g., voice, sound, etc.) input through the communication unit 350 or the input/output unit 370. In addition, the audio output unit 325 may output audio stored in the storage unit 390 under control of the control unit 380. The audio output unit 325 may include at least one of a speaker 326, a headphone output terminal 327, and a Sony/Phillips Digital Interface (S/PDIF) output terminal 328. The audio output unit 325 may include a combination of the speaker 326, the headphone output terminal 327, and the S/PDIF output terminal 328.

The audio output unit 325 may be an earphone type so that the audio output unit 325 is wearable over ears of the user of the HMD 100, but is not limited thereto. The audio output unit 325 may be configured to be detachable from the HMD 100, so that the audio output unit 325 is wearable over a user's ears according to a user's selection.

A plurality of electrodes may be disposed in the audio output unit 325 so as to receive ECG signals. In a case where the electrodes are disposed in the audio output unit 325, ECG signals may be received from the user through the plurality of electrodes when the user wears the HMD 100.

The audio output unit 325 may output various audios based on the ECG signals that the HMD 100 receives from the plurality of electrodes under control of the control unit 380. For example, when the control unit 380 determines that the user is not wearing the HMD 100 in a normal position, the display unit 315 may output a notice that requests the user to reposition the HMD 100.

Under control of the control unit 380, the power supply unit 330 may supply the internal elements of the HMD 100 with power received from an external power source. In addition, under control of the control unit 380, the power supply unit 330 may supply the internal elements of the HMD 100 with power output from one or more batteries (not illustrated) disposed inside the HMD 100.

The power supply unit 330 may be disposed in various parts of the HMD 100. For example, the power supply unit 330 may be disposed in the temple distal end portion.

The sensing unit 340 may sense a state of the HMD 100 or a state around the HMD 100 and transfer the sensed information to the control unit 380. The sensing unit 340 may include at least one of an ECG sensor 340-1, a magnetic sensor 341, an acceleration sensor 342, a temperature/humidity sensor 343, an infrared sensor 344, a gyroscope sensor 345, a position sensor (e.g., GPS) 346, a pressure sensor 347, a proximity sensor 348, an RGB sensor (illuminance sensor) 349, and a fingerprint sensor 340-4, but is not limited thereto.

The ECG sensor 340-1 may sense the ECG signal from the user through an electrode unit 340-2 included in the ECG sensor 340-1. When ECG signals are received through electrodes included in the electrode unit 340-2, the ECG sensor 340-1 may measure and analyze the received ECG signals and transfer the measured and analyzed ECG signals to the control unit 380.

The ECG sensor 340-1 may include a differential amplifier 340-3. The differential amplifier 340-3 may output an ECG by amplifying the difference between two inputs from the plurality of ECG signals input from the plurality of electrodes. For example, the differential amplifier 340-3 may calculate a difference value between a voltage of an ECG signal received through one electrode disposed in the temple 101 and a voltage of an ECG signal received through one electrode disposed in the nose pad 104, and amplify and output the calculated difference value. In another exemplary embodiment, the differential amplifier 340-3 may be included in the control unit 380.

In another exemplary embodiment, the differential amplifier 340-3 may also be used to remove noise based on an ECG signal received through at least one of the plurality of electrodes. For example, the differential amplifier 340-3 may calculate a difference value between a voltage of an ECG signal received through one electrode disposed in the temple 101 and a voltage of an ECG signal received through one electrode disposed in the nose pad 104, and remove noise included in the calculated difference value by using an ECG signal received from the lens frame 103. In this manner, a more accurate ECG may be output. The fingerprint sensor 340-4 may sense information about a user's fingerprint from the user. The sensing unit 340 may include all or part of the above-mentioned sensors.

In addition, the sensing unit 340 may include a sensor configured to sense a touch input by an input tool and a sensor configured to sense a touch input by the user. In this case, the sensor configured to sense the touch input by the user may be included in a touch screen or a touch pad. In addition, the sensor configured to sense the touch input by the input tool may be positioned under the touch screen or the touch pad, or may be included in the touch screen or the touch pad.

The communication unit 350 may connect the HMD 100 to an external device (e.g., an audio device, etc.) under control of the control unit 380. The control unit 380 may transmit and receive content with the external device connected through the communication unit 350, or may download an application from the external device or perform web browsing.

The communication unit 350 may include at least one of a wireless local area network (WLAN) 351 and a Bluetooth 352 according to the performance and configuration of the HMD 100. The communication unit 350 may include a combination of the WLAN 351 and the Bluetooth 352.

The communication unit 350 may include a Bluetooth low energy (BLE) communication unit, a near field communication (NFC) unit, a WLAN (Wi-Fi) communication unit, a ZigBee communication unit, an infrared data association (IrDA) communication unit, a Wi-Fi direction (WFD) communication unit, an ultra-wideband (UWB) communication unit, and an Ant+ communication unit, but the inventive concept is not limited thereto.

The communication unit 350 may transmit and receive a wireless signal with at least one of a base station, an external terminal, and a server via a mobile communication network. The wireless signal may include a voice call signal, a video call signal, or various types of data according to transmission and reception of text and multimedia messages.

The communication unit 350 may include a broadcasting reception unit configured to receive broadcasting signals and/or broadcasting-related information from the outside via a broadcasting channel. The broadcasting channel may include a satellite channel and a terrestrial channel.

The communication unit 350 may receive a control signal from an external controller under control of the control unit 380. The control signal may be communicated via Bluetooth, Wi-Fi, or some other mode of communication using RF signals.

The communication unit 350 may communicate with an external audio device under control of the control unit 380. In particular, in some exemplary embodiments, the communication unit 350 may include a BLE communication unit and a WLAN (Wi-Fi) communication unit and may transmit and receive a predetermined control signal with an external audio device located within a predetermined distance.

The detection unit 360 may detect a voice of the user, an image of the user, or a reaction of the user.

The microphone 361 may receive an audio input from the user. The microphone 361 may convert the received input into an electrical signal and output the electrical signal to the control unit 380. The audio input of the user may include a voice corresponding to a menu or a function of the HMD 100. A recognition range of the microphone 361 may be to about 4 m to the user. The recognition range of the microphone 361 may be changed according to a voice volume of the user and surrounding environments (e.g., speaker sound, ambient noise, etc.).

The microphone 361 may be integrally formed with the HMD 100 or may be formed separately from the HMD 100. The separate microphone 361 may be electrically connected to the HMD 100 through the communication unit 350 or the input/output unit 370.

It will be easily understood by a person of ordinary skill in the art that the microphone 361 may be excluded according to the performance and configuration of the HMD 100.

The imaging unit 362 may include a lens (not illustrated) and an image sensor (not illustrated). The imaging unit 362 may support optical zoom or digital zoom by using a plurality of lenses and/or image processing. A recognition range of the imaging unit 362 may be variably set according to an angle of a camera and surrounding environment conditions. When the imaging unit 362 includes a plurality of cameras, the imaging unit 362 may receive a 3D still image or a 3D motion by using the plurality of cameras.

The imaging unit 362 may include an infrared camera and a TOF camera.

The imaging unit 362 may further include an illumination unit (not illustrated). For example, the imaging unit 362 may include at least one of a visible-ray illumination unit (not illustrated) configured to acquire light reflected from a subject with respect to a visible-ray light source and an infrared-ray illumination unit (not illustrated) configured to acquire light reflected from a subject with respect to an infrared-ray light source. Either of the visible-ray illumination unit and the infrared-ray illumination unit may be appropriately selected as the illumination unit to use for a situation according to characteristics of the subject and a size of the subject.

The imaging unit 362 may be disposed on the lens 102 or the lens frame 103. Alternatively, the HMD 100 may include a plurality of imaging units 362. For example, at least one imaging unit may be additionally disposed in the HMD 100 so as to capture an image of the user's iris. In this case, the additional imaging unit(s) may be disposed inside the lens frame 103 to capture the iris image.

The imaging unit 362 may be integrally formed with the HMD 100 or may be formed separately from the HMD 100. A separate device (not illustrated) including the separate imaging unit 362 may be electrically connected to the HMD 100 through the communication unit 350 and/or the input/output unit 370.

The imaging unit 362 may acquire an image of the user's iris. The imaging unit 362 may acquire multiple images of the user's iris to form a combined partial image of the iris. Acquisition of further iris images may stop when the ratio of a region corresponding to the combined partial image to the entire iris reaches a preset threshold value or more.

The imaging unit 362 may capture the iris image twice or more at preset periods.

The imaging unit 362 may have previously captured partial images of the iris two or more times prior to occurrence of a predetermined event necessary for user authentication.

The input/output unit 370 may receive video (e.g., a moving image, etc.), audio (e.g., a voice, a sound, etc.), and additional information (e.g., an electronic program guide (EPG), etc.) from the outside of the HMD 100 under control of the control unit 380. The input/output unit 370 may include one of a high-definition multimedia interface (HDMI) port 371, a component jack 372, an input unit 373, and a universal serial bus (USB) port 374. The input/output unit 370 may include a combination of the HDMI port 371, the component jack 372, the input unit 373, and the USB port 374. The input unit 373 may include a plurality of keys configured to receive number or text information and set various functions. These keys may include a menu key, a screen on/off key, a power on/off key, and a volume control key. The input unit 373 may generate a key event associated with a user setting and a function control of the HMD 100 and transfer the key event to the control unit 380.

It will be easily understood by a person of ordinary skill in the art that the configuration and operation of the input/output unit 370 may be implemented in various ways in various embodiments of the inventive concept.

The control unit 380 may control the overall operation of the HMD 100 and the signal flow between the internal elements of the HMD 100 and perform data processing. When a user input is received or a pre-stored condition is satisfied, the control unit 380 may execute an operating system (OS) and/or various applications stored in the storage unit 390.

The control unit 380 may include random access memory (RAM) 381 configured to store a signal or data input from the outside of the HMD 100 and/or used as storage regions corresponding to various operations performed by the HMD 100, read-only memory (ROM) 382 configured to store a control program for controlling the HMD 100, and a processor 383.

The processor 383 may include a graphic processing unit (GPU) for graphic processing corresponding to video. Although shown separately as GPU 384, the GPU 384 may be integrated with the processor 383. The processor 383 may be implemented as a system on chip (SoC) in which a core (not illustrated) and a GPU are integrated. The processor 383 may be a single core, a dual core, a triple core, a quad core, or some multi-core processor.

The processor 383 may include a plurality of processors. For example, the processor 383 may include a main processor (not illustrated) and a sub processor (not illustrated) configured to operate in a sleep mode.

The GPU 384 may generate a screen including various objects, such as an icon, an image, or a text, by using an arithmetic unit (not illustrated) and a rendering unit (not illustrated). The arithmetic unit may calculate attribute values such as coordinate values, shapes, sizes, and colors of the objects, according to the layout of the screen by using the user reaction detected by the detection unit 160. The rendering unit may generate screens of various layouts including the objects based on the attribute values calculated by the arithmetic unit. The screens generated by the rendering unit may be displayed in a display region of the display unit 115.

A plurality of interfaces 385-1 to 385-n may be connected to the above-described elements.

The RAM 381, the ROM 382, the processor 383, the GPU 384, and the interfaces 385-1 to 385-n may be mutually connected via internal buses.

The term "control unit" used herein may include the processor 383, the ROM 382, and the RAM 381.

The control unit 380 of the HMD 100 may generate a normalized image for user authentication by combining partial images acquired by the imaging unit 362.

The control unit 380 determines whether the partial images acquired by the imaging unit 362 include at least one of an outer contour line and an inner contour line of the iris and determine whether the partial images are enough to generate the normalized image. The control unit 380 may generate the normalized image from a combined partial image determined to be sufficient for generation of the normalized image.

The control unit 380 may determine a position occupied in the normalized image by each of the partial images acquired through the imaging unit 362 and combine the partial images based on the determined position.

When a predetermined event requiring user authentication occurs, the control unit 380 may authenticate the user by using the generated normalized image.

The control unit 380 may authenticate the user by comparing an entire iris image pre-stored in the storage unit 390 with the generated normalized image.

When the partial images acquired by the imaging unit 362 include the outer contour line of the iris, the control unit 380 may estimate the size of the iris from a radius of a virtual circle including the outer contour line by using a curvature of the outer contour line.

When the partial images acquired by the imaging unit 362 include the inner contour line of the iris, the control unit 380 may estimate a size of a pupil from a radius of a virtual circle including the inner contour line by using a curvature of the inner contour line.

When the capturing distances of the partial images acquired by the imaging unit 362 are different from one another, the control unit 380 may adjust the size of the acquired partial images based on the capturing distances.

The control unit 380 may perform correction processing on the partial images acquired through the imaging unit 362, the correction processing including at least one of gamma correction, contrast correction, and sharpness correction.

When a predetermined event requiring user authentication occurs, the control unit 380 may provide a UI for capturing the iris of the user.

The control unit 380 may provide a UI for guiding a user's eye to look at specific positions to acquire partial images of the iris, including a position to acquire an image of the entire iris if possible.

It will be easily understood by a person of ordinary skill in the art that the configuration and operation of the control unit 380 may be implemented in various ways according to exemplary embodiments.

The storage unit 390 may store various data, programs, and/or applications for operation of the HMD 100 under control of the control unit 380. The storage unit 390 may store input/output signals or data corresponding to operation of the video processing unit 310, the display unit 315, the audio processing unit 320, the audio output unit 325, the power supply unit 330, the communication unit 350, the detection unit 360, and the input/output unit 370. The storage unit 390 may store a control program for controlling the HMD 100 and the control unit 380, an application initially provided by a manufacturer or downloaded from the outside, a GUI associated with the application, an object (e.g., an image text, an icon, a button, etc.) for providing the GUI, user information, a text, databases, or related data.

The term "storage unit" used herein may include a memory card (e.g., a micro secure digital (SD) card, a USB memory, etc.) (not illustrated) mounted on the storage unit 390, the ROM 182, the RAM 181, or the HMD 100. The storage unit 390 may include non-volatile memory, volatile memory, a hard disk drive (HDD), or a solid state drive (SSD).

Although not illustrated, the storage unit 390 may include a broadcasting reception module, a channel control module, a volume control module, a communication control module, a speech recognition module, a motion recognition module, a light reception module, a display control module, an audio control module, an external input control module, a power control module, a power control module of an external device connected by wireless (e.g., Bluetooth), a voice database, or a motion database. These modules and databases may be implemented by software so as to execute a broadcasting reception control function, a channel control function, a volume control function, a communication control function, a speech recognition function, a motion recognition function, a light reception control function, a display control function, an audio control function, an external input control function, a power control function, and a power control function of an external device connected by wireless (e.g., Bluetooth) in the HMD 100. The control unit 380 may execute the functions by using the software stored in the storage unit 390.

The storage unit 390 may have pre-stored the entire iris image of the user.

The storage unit 390 may store a plurality of iris images of the user that are acquired through the imaging unit 362.

The storage unit 390 may store a variety of biometric information for user authentication. When ECG signals are received through the plurality of electrodes disposed in the HMD 100 under control of the control unit 380, the storage unit 390 may store at least one ECG signal to be compared with the received ECG signals. The storage unit 390 may pre-store (or preregister) at least one ECG signal to be compared with the ECG signals received for user authentication under control of the control unit 380.

In another exemplary embodiment, the storage unit 390 may pre-store biometric information, such as information about a user's fingerprint, information about a user's iris, and information about a user's pulse, as objects to be compared for user authentication. However, the biometric information is not limited to the above-mentioned information, and the biometric information may include any information available for user authentication.

At least one of the elements (e.g., elements labeled 301 to 390) included in the HMD 100 of FIGS. 3A and 3B may be removed, and other element(s) not specifically shown in FIGS. 3A and 3B may be added to the HMD 100. It will be easily understood by a person of ordinary skill in the art that the positions of the elements shown in FIGS. 3A and 3B may be changed according to the performance requirements and/or various configurations of the HMD 100.

Figure 4:
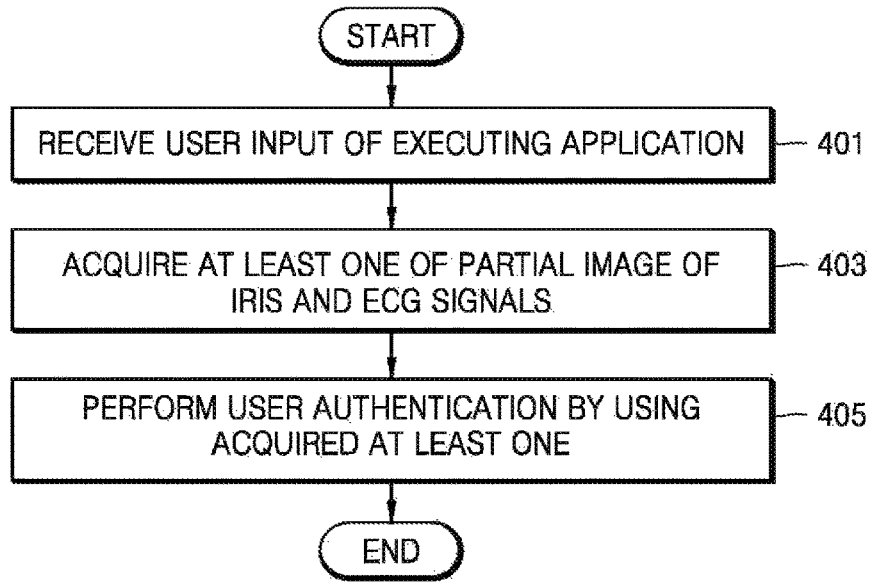
FIG. 4 is a flowchart of a user authenticating method according to an exemplary embodiment.

FIG. 4 is a flowchart of a user authenticating method according to an exemplary embodiment.

In operation 401, the control unit 380 may receive a user input to execute an application.

The control unit 380 may have set an authentication level (or security level) for an application according to a security level required by the application. For example, the control unit 380 may set a high authentication level to a financial application and an application requiring personal information protection. In another example, the control unit 380 may set a medium authentication level to an application to be charged. In another example, the control unit 380 may set a low authentication level to a screen locking application and an Internet application. However, these are only exemplary and the setting of the authentication level for the applications is not limited thereto.

In operation 403, the control unit 380 may acquire at least one of a partial image of an iris and ECG signals.

The control unit 380 may acquire a partial image of an iris from the imaging unit. In another exemplary embodiment, the control unit 380 may acquire ECG signals from the plurality of electrodes disposed in the HMD 100.

When an application execution input is received, the control unit 380 may control the imaging unit to capture a partial image of the iris. In another exemplary embodiment, the control unit 380 may access an iris image captured before the application execution input was received. For example, the control unit 380 may control the imaging unit to capture a partial image of the iris at regular time intervals and store the captured partial image of the iris in the storage unit 390. When the application execution input is received, the control unit 380 may access the stored partial region of the iris from the storage unit 390.

When the application execution input is received, the control unit 380 may acquire ECG signals through the plurality of electrodes. In another exemplary embodiment, the control unit 380 may have previously acquired the ECG signals before the application execution input is received. For example, the control unit 380 may receive the ECG signals through the plurality of electrodes at regular time intervals and store the received ECG signals in the storage unit 390. When the application execution input is received, the control unit 380 may acquire the received ECG signals from the storage unit 390.

In operation 405, the control unit 380 may perform user authentication by using at least one of the acquired partial images of the iris and the acquired ECG signal.

The control unit 380 may perform user authentication by using at least one of the acquired partial images of the iris and the acquired ECG signal according to the authentication level set for the application to be executed.

For example, when the authentication level set for the application is high, the control unit 380 may perform user authentication by using both the iris images and the ECG signal. When the authentication level set for the application is medium, the control unit 380 may perform user authentication by using the iris images. When the authentication level set for the application is low, the control unit 380 may perform user authentication by using the ECG signal. However, these are only exemplary and various embodiments of the inventive concept are not limited thereto.

The control unit 380 may set each application to perform user authentication by using at least one of the iris images and the ECG signal. For example, the control unit 380 may set each application to perform user authentication by using both or either of the iris images and the ECG signal.

The control unit 380 may perform user authentication according to whether both or either of the iris images and the ECG signal are acquired.

When both the iris images and the ECG signal are acquired, the control unit 380 may perform user authentication by using the partial images of the iris and the ECG signal. In another example, when both partial iris images and ECG signal are acquired, the control unit 380 may perform user authentication by using both the iris images and the ECG signal, regardless of the authentication level set for the application to be executed.

When only the ECG signal is acquired, the control unit 380 may perform user authentication according to the authentication level set for the application. For example, the control unit 380 may control the imaging unit to acquire the iris image with respect to the application for which the high authentication level is set. In another example, the control unit 380 may perform user authentication by using only the ECG signal with respect to the application for which the medium authentication level is set. In another example, the control unit 380 may control the imaging unit to capture the partial image of the iris with respect to the application for which the medium authentication level is set, and perform user authentication by using the partial image of the iris acquired by the capturing. In another example, the control unit 380 may perform user authentication by using only the ECG signal with respect to the application for which the low authentication level is set.

When only the partial image of the iris is acquired, the control unit 380 may perform user authentication according to the authentication level set for the application. For example, the control unit 380 may perform user authentication by using only the acquired partial image of the iris with respect to the application for which the high authentication level is set. In another example, the control unit 380 may control the ECG sensor to acquire the ECG signal with respect to the application for which the high authentication level is set. When the ECG signal is acquired, the control unit 380 may perform user authentication based on the acquired ECG signal and the acquired partial image of the iris. In another example, the control unit 380 may perform user authentication by using the acquired partial image of the iris with respect to the application for which the medium authentication level is set and the application for which the low authentication level is set.

Hereinafter, exemplary embodiments that use iris images as biometric information for user authentication will be described with reference to FIGS. 5 to 16, and exemplary embodiments that use ECG signals as biometric information for user authentication will be described with reference to FIGS. 17 to 28.

Figure 5:
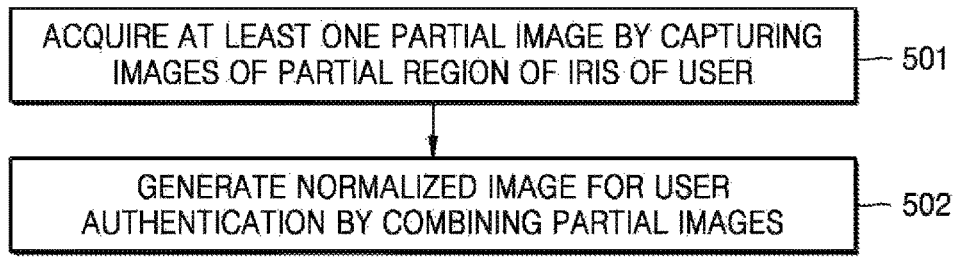
FIGS. 5 to 7 are flowcharts of methods of controlling an HMD, according to exemplary embodiments.
Figure 6:
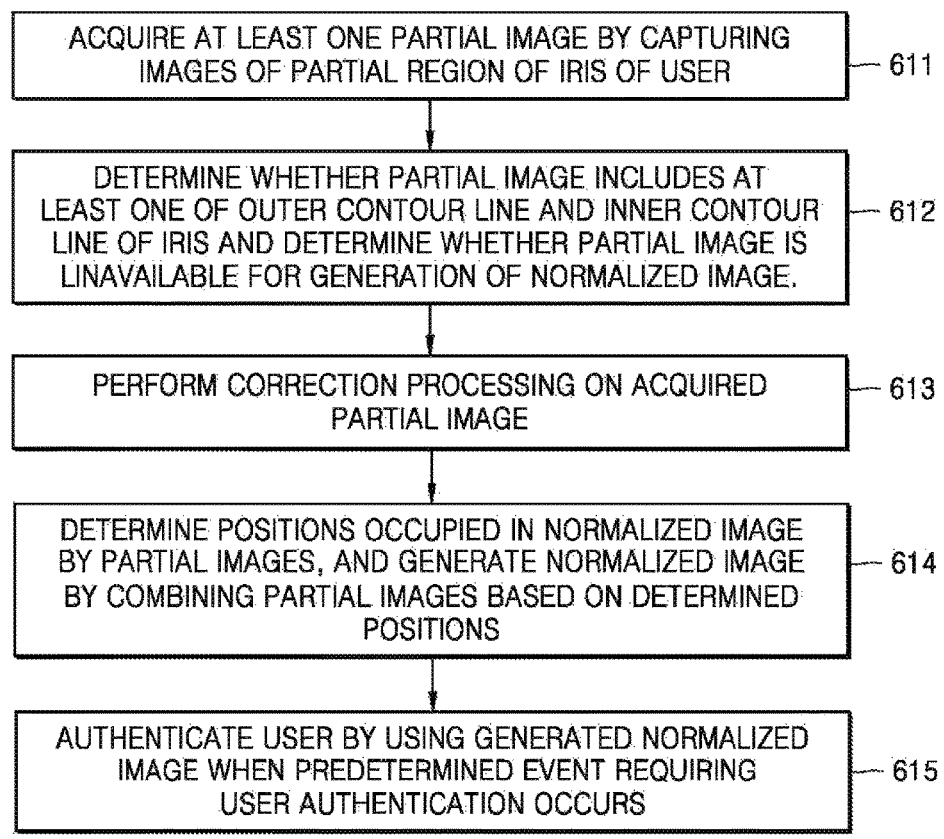
Figure 7:
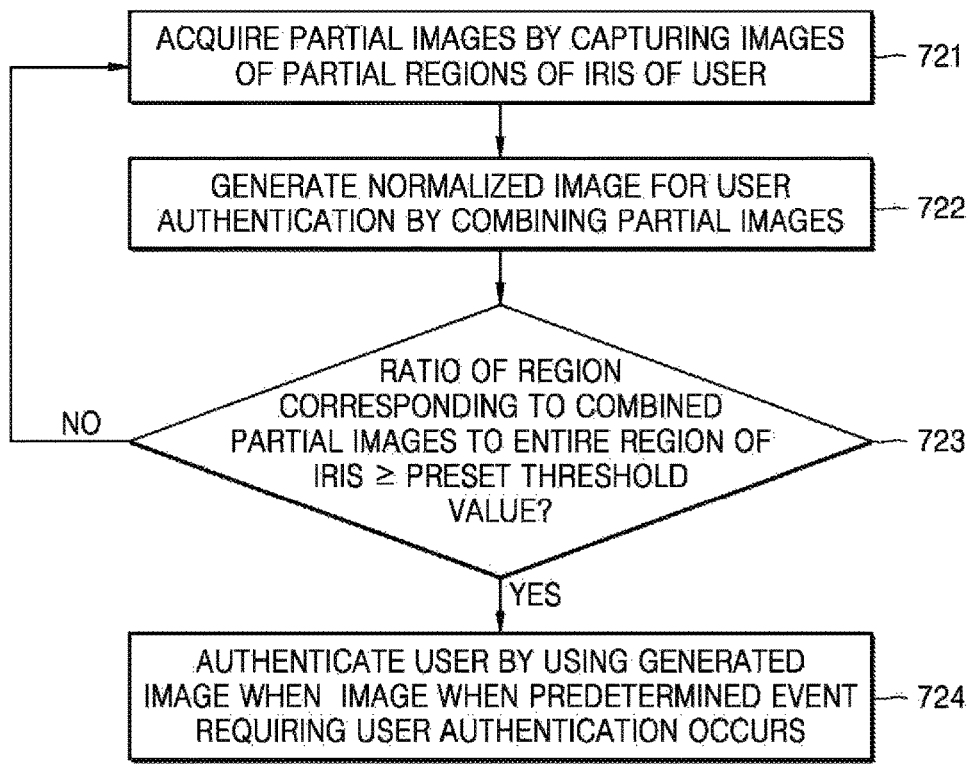

FIGS. 5 to 7 are flowcharts of methods of controlling an HMD 100, according to an exemplary embodiment. FIGS. 8 to 16 will also be referred to in the following description for FIGS. 5 to 7.

The HMD 100 according to the various exemplary embodiments may be applicable to user authentication by using an iris image to generate a normalized image through a combination of a plurality of partial images acquired by capturing partial regions of the iris.

In the case of the HMD 100, since a capturing distance between the imaging unit and the user's eye is short, it may be difficult to acquire an entire image of the iris at one time. According to an exemplary embodiment, even when the iris image is partially acquired, the entire iris image may be generated by combining a plurality of partial iris images.

In the present disclosure, a normalized image may mean an image acquired by combining a plurality of partial images.

Referring to FIG. 5, in operation 501, the imaging unit 362 of the HMD 100 may acquire at least one partial image by capturing a partial region of an iris of a user.

In operation 502, the control unit 380 of the HMD 100 may generate a normalized image for user authentication by combining the partial images acquired in operation 501. The operation of generating the normalized image by combining the partial images will be described in detail with reference to FIG. 6.

The imaging unit 362 of the HMD 100 may capture an iris image of the user twice or more at preset periods.

The imaging unit 362 may capture the iris image of the user two or more times based on a remaining battery level of the HMD 100. For example, when the remaining battery level of the HMD 100 is equal to or greater than a preset threshold value, the iris image of the user may be captured more frequently than when the remaining battery level of the HMD 100 is less than the preset threshold value.

The imaging unit 362 may capture partial images of the user's iris two or more times until a ratio of a region of the iris corresponding to the combined partial image formed by combining the partial images by the control unit 380 to the entire iris reaches or exceeds a preset threshold value.

The imaging unit 362 may have previously captured partial images of the iris prior to occurrence of a predetermined event requiring user authentication. When the predetermined event requiring user authentication occurs, the control unit 380 may authenticate the user by using the generated normalized image. The occurrence of the predetermined event may be, for example, an execution of an Internet banking application, a request for login of a specific Internet site, or a request for unlocking the display screen, but is not limited thereto.

For example, when the user wears the glass-type wearable HMD 100, the control unit 308 may automatically acquire the iris image of the user at regular periods without the user's input and store the iris images in the storage unit 390. Thus, the iris image of the user may be used later when the user authentication is required. That is, since the HMD 100 intermittently acquires the iris image without user's knowledge, user authentication may be performed automatically.

In another exemplary embodiment, when a predetermined event requiring user authentication occurs, the control unit 380 may provide a UI for acquiring the iris image of the user. For example, when an Internet banking application having a high security level and requiring user authentication is executed, the HMD 100 may provide the UI for acquiring the iris image of the user to the display unit 315.

Figure 8:
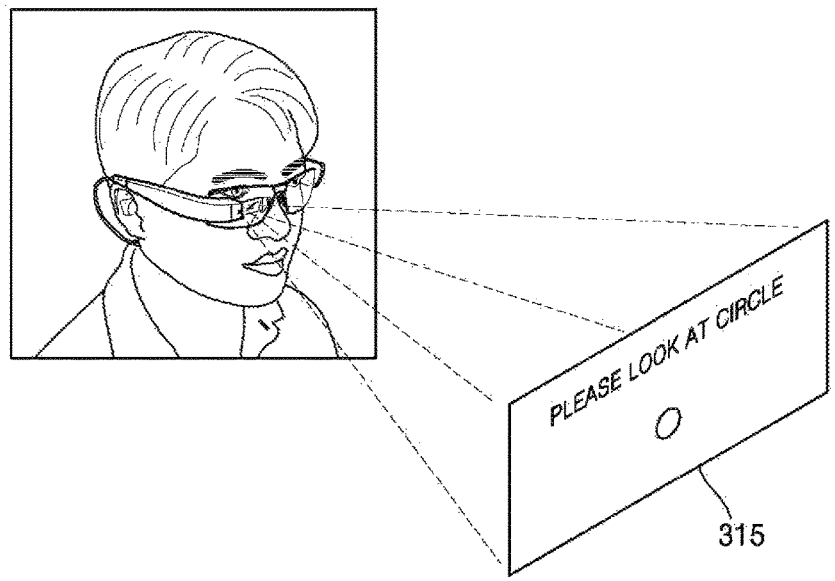
FIG. 8 is a diagram for describing an example of a user interface for acquiring an image of a user's iris, according to an exemplary embodiment.

For example, as illustrated in FIG. 8, the control unit 380 may control the display unit 315 to display a screen showing a position to be looked at by the user so as to capture an appropriate iris image of the user.

In addition, the control unit 380 may output audio guidance through the audio output unit 325 to warn the user from blinking during image capture of the iris, but is not limited thereto.

FIG. 6 is a flowchart of a method of controlling the HMD 100, according to an exemplary embodiment.

Referring to FIG. 6, in operation 611, the imaging unit 362 of the HMD 100 may acquire at least one partial image by capturing images of a partial region of an iris of a user. Since acquiring the iris image of the user is substantially identical to operation 501 of FIG. 5, detailed description thereof will be omitted. In operation 612, the control unit 380 of the HMD 100 may determine whether the partial image acquired in operation 611 includes at least one of an outer contour line and an inner contour line of the iris and may determine whether the partial image acquired in operation 611 is sufficient for the generation of a normalized image.

Various descriptions will now be made with reference to FIGS. 9 to 15 to explain the process for generating the normalized image.

Figure 9:
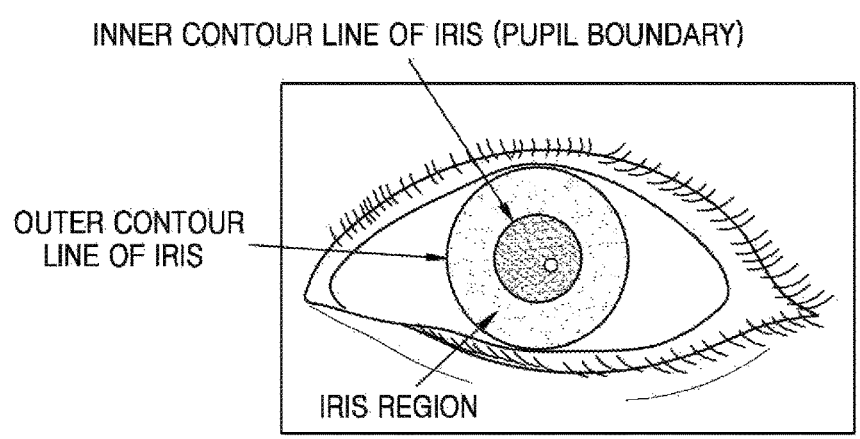
FIG. 9 is a diagram for describing an iris region.

Referring to FIG. 9, the iris region is a donut-shaped muscle tissue disposed between the pupil and the sclera (white part of the eye). In order to extract the iris region, it is necessary detect the pupil boundary and the boundary between the sclera and the iris. The pupil boundary means the inner contour line of the iris, and the boundary of the sclera and the iris tissue means the outer contour line of the iris.

Figure 10:
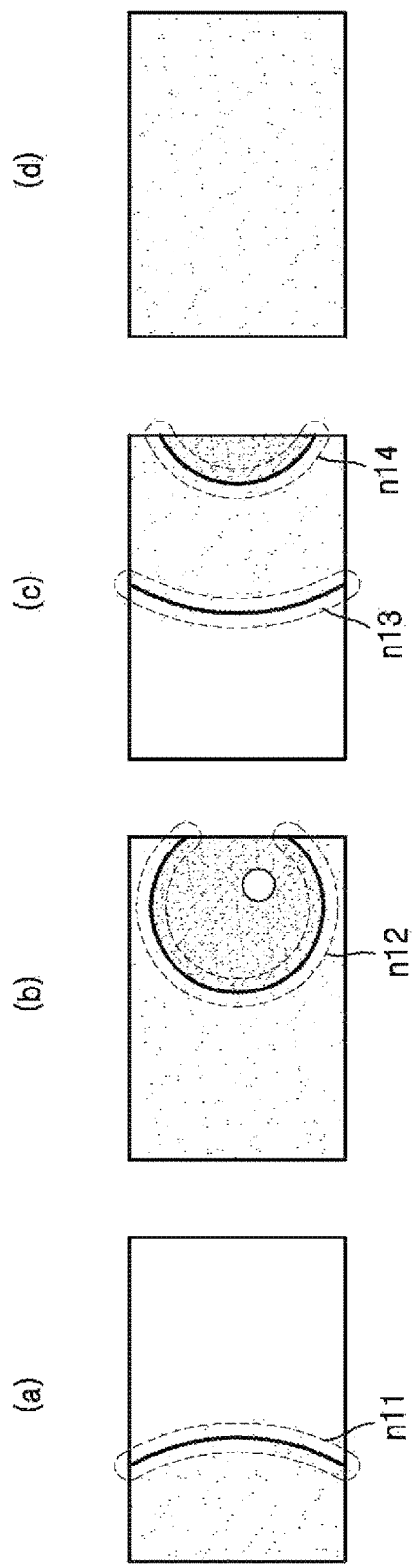

FIG. 10 is a diagram for describing examples of the partial image of the iris. Referring to FIG. 10, the partial image acquired by capturing the partial region of the iris may be image (a) that includes only an outer contour line n11 of the iris, an image (b) that includes only an inner contour line n12 of the iris, or an image (c) that includes both an inner contour line n14 and an outer contour line n13 of the iris. In addition, the partial image may be an image (d) that includes neither an inner contour line nor an outer contour line of the iris.

FIG. 11 is a table that lists whether a normalized image can be generated from one of the partial images shown in FIG. 10. Sections (a) to (d) of FIG. 11 describe whether a partial image is sufficient for generation of the normalized image. If a partial image is not enough, it may be combined with successively acquired partial images until the combined partial image is enough to generate a normalized image.

The control unit 380 of the HMD 100 may determine whether the partial image includes at least one of the outer contour line and the inner contour line of the iris and may determine whether the partial image is sufficient for generation of the normalized image. In a case where the boundary line of the iris (the outer contour line or the inner contour line) is included in the partial image of the iris, the control unit 380 may extract a virtual circle including the boundary line by using a curvature of the boundary line, and calculate a radius of the virtual circle.

Referring to FIG. 11, in the case of a partial image including only the outer contour line of the iris ((a) of FIG. 11), a virtual circle defined by the outer contour line may be extracted by using a curvature of the outer contour line of the iris. A radius of the virtual circle defined by the outer contour line of the iris is a radius of the iris, and the size of the iris may be estimated from the radius of the virtual circle.

However, in the case of the image including only the outer contour line of the iris, since there is no way to know the position of the pupil defined by the inner contour line of the iris, it may be difficult to use the corresponding image for the generation of the normalized image. On the other hand, when it is possible to determine the position of the pupil by using additional partial images, addition of information from the image including only the outer contour line may be usable for generation of the normalized image.

In the case of a partial image including only the inner contour line of the iris ((b) of FIG. 11), a virtual circle including the inner contour line may be extracted by using a curvature of the inner contour line of the iris. A radius of the virtual circle defined by the inner contour line of the iris may be a radius of the pupil.

At this time, when it is possible to acquire information about the size of the iris, the control unit 380 may extract the outer contour line of the iris by using the information about the size of the iris, with reference to the central point of the circle including the inner contour line of the iris. In this case, the partial image including only the inner contour line of the iris may be enough to generate the normalized image.

In the case of a partial image including both the outer contour line and the inner contour line of the iris ((c) of FIG. 11), a virtual circle including the outer contour line may be estimated by using a curvature of the outer contour line of the iris, and a virtual circle including the inner contour line may be estimated by using a curvature of the inner contour line of the iris.

In addition, the size of the iris may be estimated by using the virtual circle including the outer contour line of the iris. In addition, the size of the pupil may be estimated by using the virtual circle including the inner contour line of the iris. Therefore, the partial image including both the inner contour line and the outer contour line of the iris may be used for the generation of the normalized image.

In the case of a partial image including no boundary line of the iris ((d) of FIG. 11), it may be not be possible to estimate either the inner contour line or the outer contour line. Thus, additional iris images will be needed to generate a combined partial image needed to generate the normalized image.

Referring to FIGS. 12A and 12B, iris normalization may mean a process of converting the donut-shaped region (see FIG. 12A), except for the pupil part, from the circular shape formed by the outer contour line of the iris to a rectangular shape (see FIG. 12B) by expanding the donut-shaped region with reference to a specific point (e.g., point a). Points a, b, and c illustrated in FIG. 12A may correspond to points a, b, and c in the normalized image illustrated in FIG. 12B.

In the case of the iris of the same person, similar patterns may be extracted from the same region, regardless of a change in the size of the iris image or the size of the pupil which may change according to the capturing distance between the imaging unit and the user or the surrounding environment such as brightness.

Figure 13:
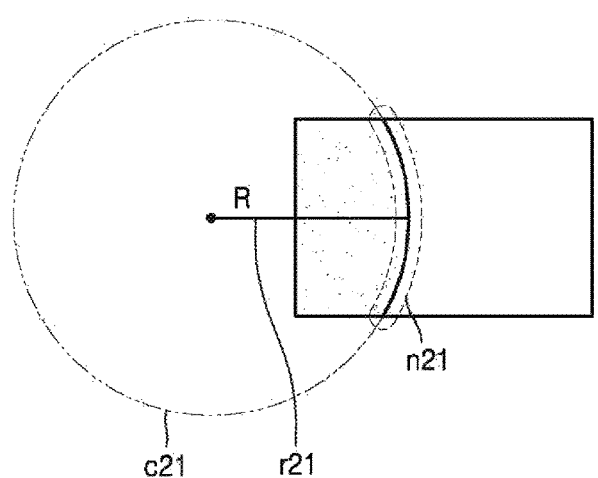
FIGS. 13 to 15 are diagrams for describing an example of determining a size of an iris from a partial image of the iris, according to an exemplary embodiment.

FIG. 13 is a diagram illustrating an example in which a partial image of an iris includes an outer contour line of the iris.

As illustrated in FIG. 13, the control unit 380 of the HMD 100 may extract a virtual circle c21 including an outer contour line n21 by using a curvature of the outer contour line n21 of the iris. In addition, the control unit 380 may calculate a radius r21 of the virtual circle c21.

Figure 14:
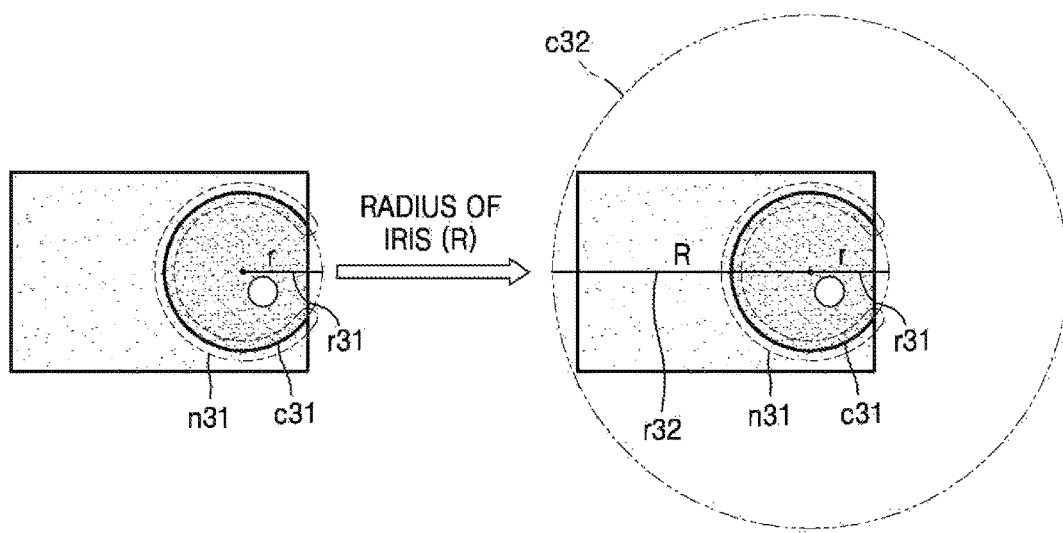

FIG. 14 is a diagram illustrating an example in which a partial image of an iris includes an inner contour line of the iris.

As illustrated in FIG. 14, the control unit 380 of the HMD 100 may extract a virtual circle c31 including an inner contour line n31 by using a curvature of the inner contour line n31 of the iris. In addition, the control unit 380 may calculate a radius r31 of the extracted virtual circle c31. The radius r31 of the virtual circle c31 defined by the inner contour line n31 may mean a radius of a pupil.

In a case where iris radius information R is acquired, the control unit 380 may extract a virtual circle c32 defined by the outer contour line of the iris by using the iris radius information R. At this time, the control unit 380 may acquire the iris radius information R by searching for another iris image or iris radius information R that is stored in the storage unit 390 in association with the same user identification information.

Figure 15:
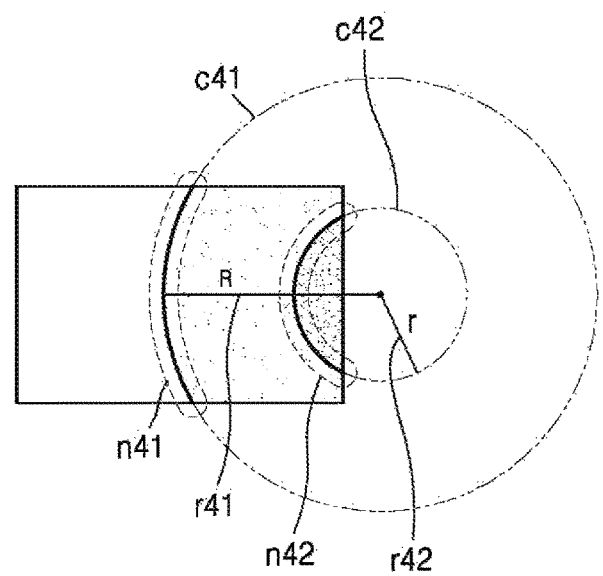

FIG. 15 is a diagram illustrating an example in which a partial image of an iris includes both an inner contour line and an outer contour line of the iris.

As illustrated in FIG. 15, the control unit 380 of the HMD 100 may extract a virtual circle c41 including an outer contour line n41 by using a curvature of the outer contour line n41 of the iris. In addition, the control unit 380 may calculate a radius r41 of the extracted virtual circle c41.

In addition, the control unit 380 may extract the virtual circle c42 including an inner contour line n42 by using a curvature of the inner contour line n42 of the iris and calculate a radius r42 of the extracted virtual circle c42. The radius r42 of the virtual circle c42 defined by the inner contour line n42 of the iris may mean a radius of a pupil.

When a donut-shaped iris region including the outer contour line n41 and the inner contour line n42 of the iris is extracted, the control unit 380 may acquire a normalized image by converting the iris region into a rectangular shape by expanding the donut-shaped iris region with reference to a specific point and may determine a position occupied in the normalized image by the partial image of the iris.

Referring to FIG. 6 again, in operation 613, the control unit 380 of the HMD 100 may perform correction processing on the iris image acquired in operation 611. The correction processing may include at least one of gamma correction, contrast correction, and sharpness correction. Therefore, the control unit 380 may acquire a clearer and more accurate iris image and may further improve accuracy in similarity determination of the iris image, which will be described below.

According to an exemplary embodiment, when the capturing distance between eyes of the user is variable, the size of the captured iris image may be different. Accordingly, the size of the iris may need to be adjusted for the capturing distance. Thus, it is necessary to perform a magnification adjustment so that each of the various images will show the iris as if the image was taken from the same capturing distance.

That is, when the capturing distances of the acquired partial images are different from one another, the control unit 380 of the HMD 100 may adjust the sizes of the plurality of iris images to adjust for the different capturing distance and normalize the iris images.

In operation 614, the control unit 380 of the HMD 100 may determine the positions occupied in the normalized image by the partial images acquired in operation 611, and generate the normalized image by combining the partial images based on the determined positions.

In order to determine the positions occupied in the normalized image by the partial images of the iris, the HMD 100 may extract virtual circles by using curvatures of the inner contour line and the outer contour line of the iris which are included in the partial images. The virtual circle including the inner contour line of the iris may be the inner contour line of the iris and the boundary line of the pupil.

In addition, the control unit 380 may perform a normalization process of converting the donut-shaped iris region, except for the pupil region, into a rectangular shape by expanding the donut-shaped iris region with reference to a specific point (see FIGS. 12A and 12B). The control unit 380 may determine the positions occupied in the normalized image by the partial images.

The control unit 380 may generate the normalized image by combining the plurality of partial images based on the determined positions.

In operation 615, when a predetermined event requiring user authentication occurs, the control unit 380 may authenticate the user by using the normalized image generated in operation 614.

The storage unit 390 of the HMD 100 may have pre-stored an entire iris image of the user.

The control unit 380 may authenticate the user by comparing the entire iris image pre-stored in the storage unit 390 with the normalized image generated in operation 614.

In general, individuals have different unique iris patterns. The control unit 380 may generate an iris code by extracting one or more feature points of a pattern appearing in the iris region and store the generated iris code. The control unit 380 may determine iris similarity by comparing the generated iris code with a pre-stored encoded iris code of the same user. When the iris patterns are determined as being similar to each other based on a predetermined criteria, the control unit 380 may determine that the user authentication has passed.

Figure 16A:
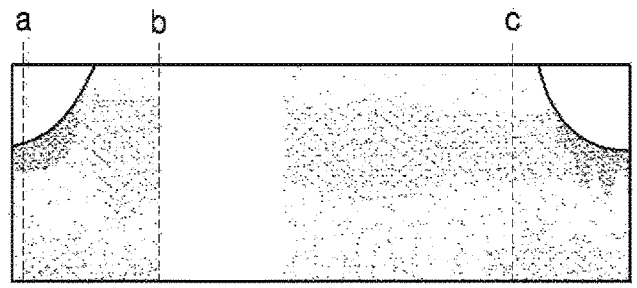
FIGS. 16A and 16B are diagrams for describing an example of user authentication using an iris image, according to an exemplary embodiment.
Figure 16B:
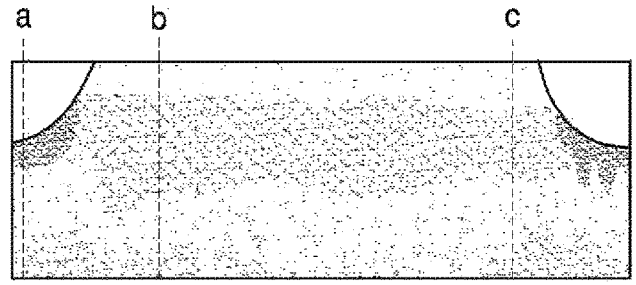

For example, as illustrated in FIG. 16A, when a normalized image generated by combining a plurality of partial images of an iris is compared with a pre-stored iris image (FIG. 16B) to which the same user identification information is assigned, it may be determined that the user authentication has passed when iris patterns are determined as similar to each other based on a predetermined criteria.

FIG. 7 is a flowchart of a method of controlling an HMD 100, according to another exemplary embodiment. Referring to FIG. 7, in operation 721, the imaging unit 362 of the HMD 100 may acquire partial images by capturing a partial region of an iris of a user. Since operation of acquiring the iris images is substantially identical to operation 501 of FIG. 5, detailed description thereof will be omitted.

In operation 722, the control unit 380 of the HMD 100 may generate a normalized image for user authentication by combining partial images acquired in operation 721. Since operation of generating the normalized image by combining the partial images has been described with reference to FIG. 6, detailed descriptions thereof will be omitted.

In operation 723, the control unit 380 of the HMD 100 may determine whether a ratio of a region corresponding to partial images combined in operation 722 to the entire iris is a preset threshold value or more.

When it is determined in operation 723 that the ratio is less than the preset threshold value, the control unit 380 may control the imaging unit 362 to further acquire the iris image of the user (721 of FIG. 7). That is, the imaging unit 362 may continue to capture the iris image of the user until the ratio of the region corresponding to the combined partial image to the entire region of the iris becomes a preset threshold value or more.

For example, when the ratio of the region corresponding to the combination of the plurality of partial images is excessively low (e.g., 50% or less with respect to the entire iris), the accuracy in the similarity determination may be low. Thus, the control unit 380 may provide a UI for further acquiring the partial image of the iris.

At this time, the control unit 380 may provide a UI for guiding the user's eye to look at a position so as to acquire partial images of the iris in the region(s) needed to generate a normalized image (see FIG. 8). The control unit 380 may also guide the user to look at position(s) from which image information is not acquired to alleviate eye strain from looking at possibly extreme positions.

In operation 724, when it is determined in operation 723 that the ratio is the preset threshold value or more, the control unit 380 of the HMD 100 may authenticate the user by using the normalized image generated in operation 722 when a predetermined event requiring user authentication occurs.

The preset threshold value may be preset according to the type of the event. For example, the preset threshold value may be set at different ratios according to the type of the application to be executed. For example, in order to authenticate the user when an Internet banking application is executed, the ratio of the region corresponding to the combination of the plurality of partial images may be set to 80% or more, while other applications may be set for lower percentages.

In another example, the preset threshold value may be preset at the same ratio, regardless of the type of the event.

Figure 17:
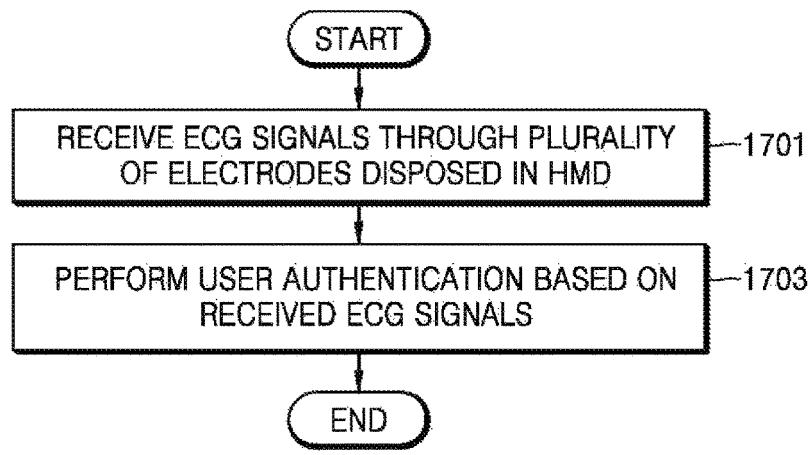
FIG. 17 is a flowchart of a user authenticating method using an ECG, according to an exemplary embodiment.

FIG. 17 is a flowchart of a user authenticating method using an ECG, according to an exemplary embodiment. Referring to FIG. 17, in operation 1701, the control unit 380 may receive ECG signals from a user from a plurality of electrodes disposed in the HMD 100. When the user wears the HMD 100, ECG signals may be received from the user through a plurality of electrodes disposed in at least one contact portion of the HMD 100 contacting the user and a non-contact portion of the HMD 100 not contacting the user.

For example, when the user wears the HMD 100, ECG signals may be received from the user through a plurality of electrodes disposed in at least one of the inner side of the temple middle portion 101-1 and the nose pad 104, which contact the user. In another example, when the user wears the HMD 100, ECG signals may be received from the user through a plurality of electrodes disposed in at least one of the outer side of the temple proximal end portion 101-2, the outer side of the temple distal end portion 101-3, and the upper side of the lens frame 103, which do not contact the user. For example, when the user touches (or contacts) the electrodes disposed in the left and right temple proximal end portions 101-2 with his or her hands, the control unit 380 may receive ECG signals from the user through the electrodes disposed in the left and right temple proximal end portions 101-2.

The control unit 380 may simultaneously receive the ECG signals through the plurality of electrodes and the input for executing the function of the HMD 100. For example, when a function button is disposed to overlap an electrode, the control unit 380 may simultaneously receive the ECG signal and the function execution input by one gesture of the user. When the electrode is disposed adjacent to the function button, for example, when the electrode and the function button are disposed in a range that is touchable by the user when the HMD 100 is touched, the control unit 380 may simultaneously receive the ECG signal and the function execution input by one gesture of the user. In another example, when the function button is the power button 117 for supplying power to the HMD 100 and the electrode is disposed adjacent to the power button 117 or disposed to be under the power button 117, the control unit 380 may simultaneously receive the ECG signal by the user touching the electrode and the power button 117. The control unit 380 may perform user authentication using the ECG signal and simultaneously execute the function corresponding to the input based on the ECG signal and the simultaneously received function execution input. However, the inventive concept is not limited thereto, and the control unit 380 may sequentially receive the ECG signal and the function execution input.

In another exemplary embodiment, when the input for executing the function of the HMD 100 is received from the user, the control unit 380 may receive ECG signals from the plurality of electrodes. For example, when the user executes the application for which authentication is required, the control unit 380 may receive ECG signal from the user so as to provide authentication for the application. For example, when the user executes an application related to financial transaction, to which an authentication using an ECG is set for security, the control unit 380 may receive ECG signals of the user from the plurality of electrodes.

While the user wears the HMD 100, the control unit 380 may periodically receive ECG signals. For example, when the HMD 100 is set to periodically receive the ECG signals, the control unit 380 may control the display unit 220 to output an ECG of the user that is measured based on the periodically received ECG signals.

The received ECG signal may be amplified. For example, the received ECG signal may be output as a signal amplified by the differential amplifier 340-3. The differential amplifier 340-3 may be separately configured or may be embedded in the control unit 380.

The control unit 380 may receive biometric signals from other sensors, as well as the plurality of electrodes receiving ECG signals from the user. For example, the control unit 380 may receive a fingerprint signal from the fingerprint sensor 340-4. In another example, the control unit 380 may receive a pulse signal from a pulse sensor (not shown). However, biometric signals received by the control unit 380 are not limited thereto, and other signals may be received by the control unit 380 as long as those signals are related to the body of the user and are measurable.

The control unit 380 may simultaneously receive the ECG signal and the biometric signals from other sensors by one gesture of the user. When electrodes are disposed to be overlapped by other sensors, the control unit 380 may simultaneously receive the ECG signals and the biometric signals from the other sensors. When electrodes are disposed on the outer surface of the HMD 100 and other sensors are embedded in the HMD 100, the control unit 380 may simultaneously receive the ECG signals and the biometric signals from the other sensors. When the electrodes are disposed adjacent to other sensors, the control unit 380 may simultaneously receive the ECG signals and the biometric signals from the other sensors. When the electrodes are disposed in a range that is simultaneously touchable with other sensors when the user touches the HMD 100, the control unit 380 may simultaneously receive the ECG signals and the biometric signals from other sensors.

When the HMD 100 is worn by the user and even when the HMD 100 is not worn by the user, the control unit 380 may control the ECG sensor 340-1 to receive the ECG signal.

In another exemplary embodiment, the control unit 380 may control the ECG sensor 340-1 to receive the ECG signal in a specific condition. For example, when power is supplied, the control unit 380 may control the ECG sensor 340-1 to receive the ECG signal during a predetermined period of time from the supply of the power. In another example, when there is a motion of the HMD 100, the control unit 380 may control the ECG sensor 340-1 to receive the ECG signal during a predetermined period of time.

For example, the HMD 100 may detect the motion of the HMD 100 through the acceleration sensor 342 or the like. Accordingly, the control unit 380 may detect that the HMD 100 is being put on the user through the acceleration sensor 342 and may control the ECG sensor 340-1 to receive the ECG signal during a predetermined period of time from the detection. In another example, the control unit 380 may detect a shaking of the HMD 100 or a change in an arranged state through the acceleration sensor 342 and control the ECG sensor 340-1 to receive the ECG signal during a predetermined period of time from the detection. This may be due to interpreting the shaking and/or moving as the HMD 100 being moved to a different person.

In operation 1703, the control unit 380 may perform user authentication based on the received ECG signal.

When the HMD 100 is locked, the control unit 380 may perform user authentication for unlocking the HMD 100 based on the received ECG signal. For example, when the locking setting of the HMD 100 is set as a user authentication using an ECG and an ECG signal is received from the user, the control unit 380 may perform user authentication using the received ECG signal and release or hold the locked state of the HMD 100 according to a user authentication result.

When an application execution input is received from the user, the control unit 380 may perform user authentication on the application based on ECG signals received through the plurality of electrodes. For example, when an input for outputting a security document is received from the user, the control unit 380 may perform user authentication set for outputting the security document.

When the ECG signals are not accurately measured, the control unit 380 may perform user authentication by using other authenticating methods. For example, the control unit 380 may measure a signal-to-noise ratio (SNR) of a received ECG signal and may perform user authentication by using other authenticating methods when the SNR of the received ECG signal is less than a preset threshold value. The SNR of the received ECG signal may be less than the preset threshold value when a waveform of the ECG signal is distorted by a user's sweat while the user wears the HMD 100.

In another exemplary embodiment, when it is impossible to perform the user authentication by using the ECG signal, the control unit 380 may perform user authentication by using other authenticating methods. For example, when a waveform of an ECG signal is distorted by a user's heavy exercise or when a waveform of an ECG signal is distorted because the user has an electronic device (e.g., a pacemaker) on the body, the control unit 380 may determine that the user authentication using the ECG signal is not reliable and perform user authentication by using other authenticating methods.

When the ECG signal is not accurately measured or when the user authentication using the ECG signal is deemed not reliable, the control unit 380 may authenticate the user through other biometric signals such as, for example, fingerprint, etc., and not preset touch input (e.g., a double tap, a swipe, etc.), text input through eye tracking, or voice input.

The control unit 380 may control the communication unit 350 to transmit the measured ECG signal to an external electronic device. In another exemplary embodiment, the control unit 380 may control the communication unit 350 to transmit a user authentication execution result to an external electronic device. In another exemplary embodiment, the control unit 380 may control the communication unit 350 to transmit at least one of the ECG signal and the user authentication execution result to a server that provides a service requiring authentication. In another exemplary embodiment, the control unit 380 may use at least one of the ECG signal and the user authentication execution result for the purpose of single sign-on (SSO) authentication.

A user authenticating method using ECG signals received through a plurality of electrodes will be described with reference to FIGS. 18 and 19. Terms used below with respect to ECG include the well-known QRS group of 3 signal points Q, R, and S. The QRS group may be preceded by the P wave and followed by the T wave.

Figure 18:
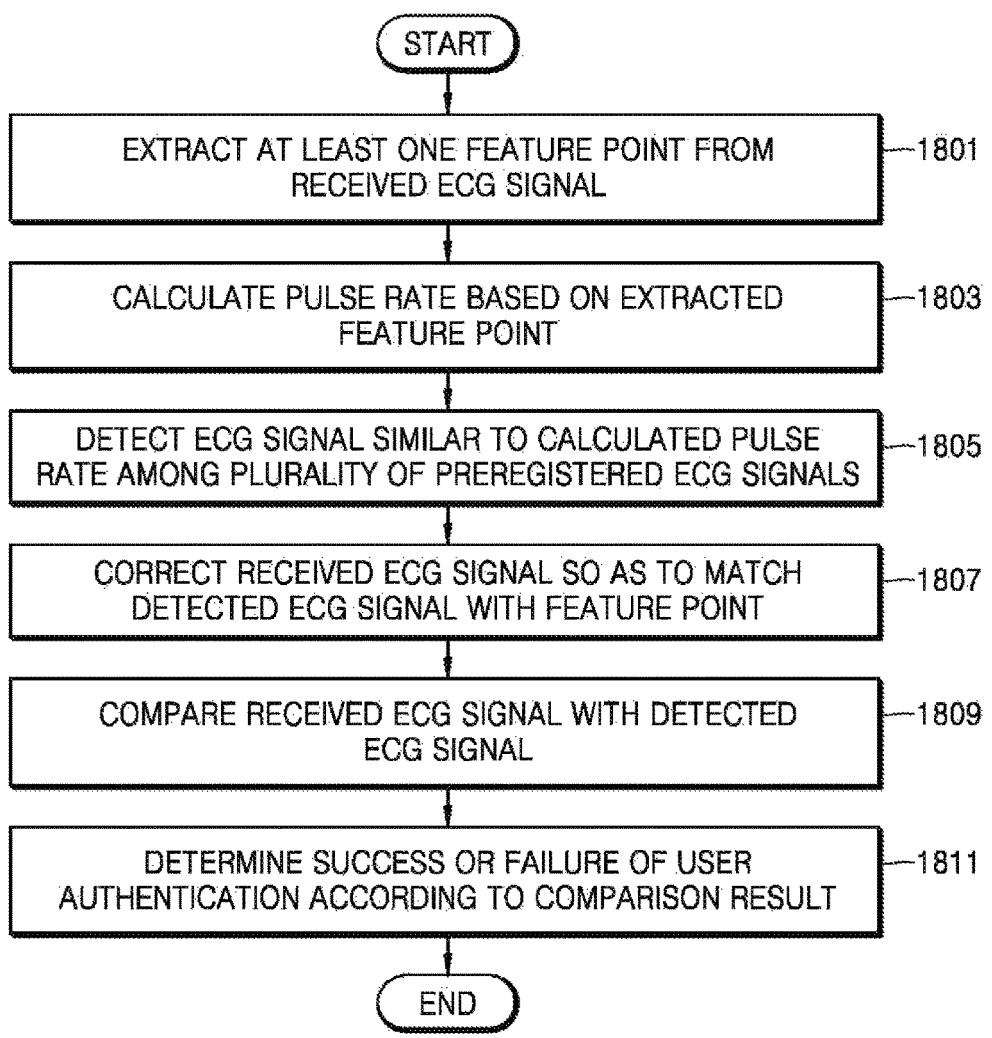
FIG. 18 is a flowchart of a user authenticating method based on ECG signals received through a plurality of electrodes, according to an exemplary embodiment.

FIG. 18 is a flowchart of a user authenticating method based on ECG signals received through a plurality of electrodes, according to an exemplary embodiment.

Figure 19:
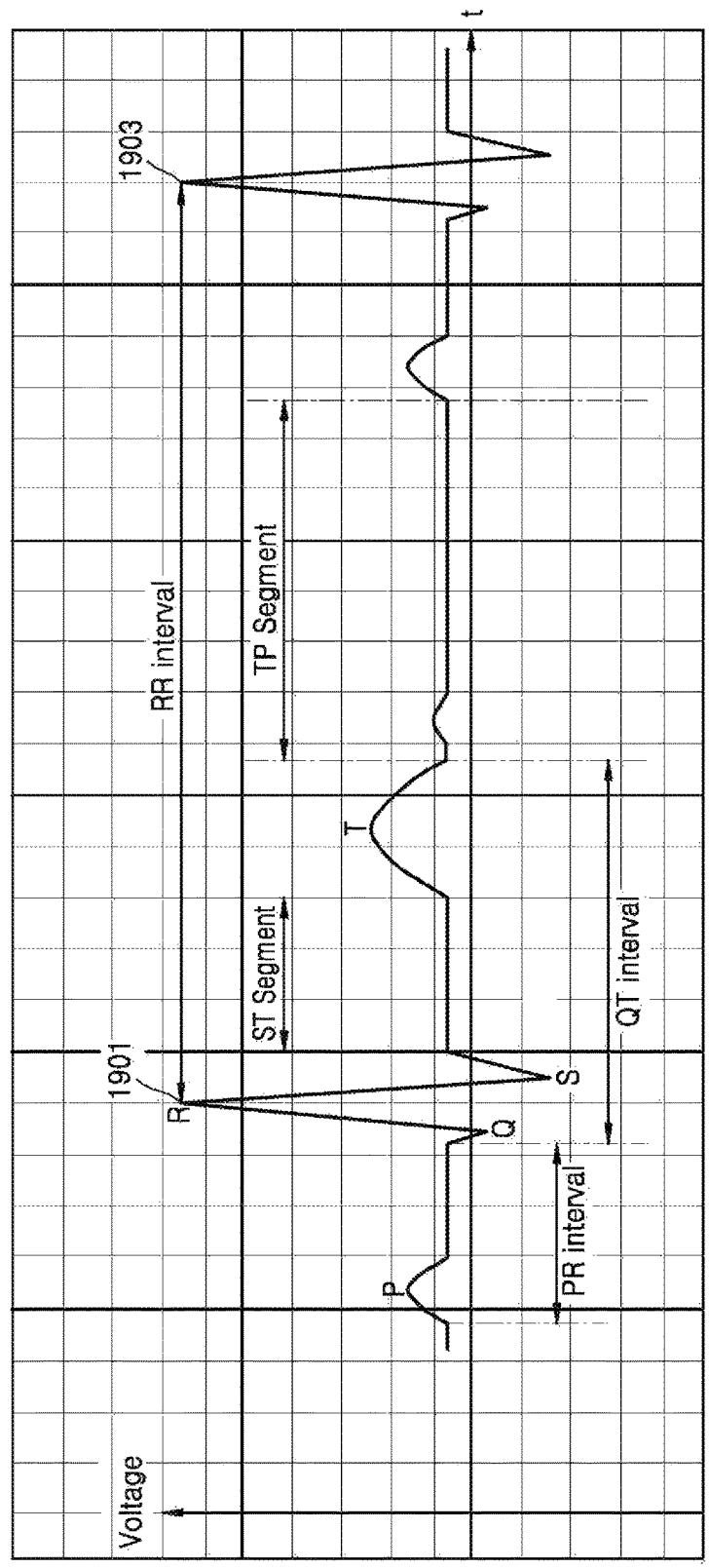
FIG. 19 is a graph showing an ECG measured from ECG signals received through a plurality of electrodes, according to an exemplary embodiment.

FIG. 19 is a graph showing an ECG measured from the ECG signals received through the plurality of electrodes, according to an exemplary embodiment.

Referring to FIGS. 18 and 19, in operation 1801, the control unit 380 may extract at least one feature point so as to calculate a pulse rate from received ECG signals. For example, the control unit 380 may extract an R point 1901 at which a voltage of a QRS group is maximum in FIG. 19 and an R point 1903 at which a voltage of a QRS group of a pulse of a next period is maximum in FIG. 19. In another example, the control unit 380 may extract, as feature points, a point at which a P wave starts and a point at which a P wave of a pulse of a next period starts. However, the inventive concept is not limited thereto. Various points or intervals for calculating the pulse rate may be extracted as feature points.

In operation 1803, the control unit 380 may calculate the pulse rate based on the extracted feature points. For example, when the R point 1901 and the R point 1903 are extracted as the feature points, the control unit 380 may measure a time corresponding to an RR interval between the R point 1901 and the R point 1903 and calculate the pulse rate based on the measured time. For example, when the RR interval is 0.6 second, the pulse rate may be calculated as 1.67 times per second or 100 times per minute. In another example, the pulse rate may be the time corresponding to the RR interval. In another example, when other points or intervals, except for the RR interval, are extracted as the feature points, the control unit 380 may calculate the pulse rate based on the extracted points or intervals.

In operation 1805, the control unit 380 may find an ECG signal that is similar to the pulse rate calculated in operation 1803 from among a plurality of preregistered ECG signals. For example, the control unit 380 may compare the calculated pulse rate with the plurality of preregistered ECG signals stored in the storage unit 390. From a comparison result, the control unit 380 may find an ECG signal that has a pulse rate most similar to the calculated pulse rate from among the plurality of preregistered ECG signals. For example, the control unit 380 may find an ECG signal with an RR interval most similar to the calculated RR interval from among the plurality of preregistered ECG signals.

In operation 1807, the control unit 380 may correct the received ECG signal so as to match the ECG signal found in operation 1805 with the feature point. The control unit 380 may perform correction so as to match a reference point for comparing the found ECG signal with the received ECG signal. For example, when the feature point of the found ECG signal is the R point, the control unit 380 may correct the feature point of the received ECG signal to the R point. In another example, the control unit 380 may correct a base line or an isoelectric line of the received ECG signal so as to match a base line or an isoelectric line of the found ECG signal. However, the inventive concept is not limited thereto. Various methods (or algorithms) for comparing the found ECG signal and the received ECG signal may be used.

In operation 1809, the control unit 380 may compare the received ECG signal with the found ECG signal. For example, the control unit 380 may compare a waveform of the received ECG signal with a waveform of the found ECG signal.

The control unit 380 may compare at least one of a voltage of the R point, a length of the PR interval, a length of a QT interval, a length of an ST segment, and a length of a TP segment and may determine a matching rate between the waveform of the received ECG signal and the waveform of the found ECG signal based on a comparison result. However, the inventive concept is not limited thereto. A length of each interval of the ECG signal, a point where the voltage is maximum, and a slope of the waveform may be a comparison reference between the waveform of the received ECG signal and the waveform of the found ECG signal.

In operation 1811, the control unit 380 may determine success or failure of the user authentication according to the comparison between the waveform of the received ECG signal and the waveform of the found ECG signal. For example, when the matching rate between the waveform of the received ECG signal and the waveform of the found ECG signal is a predetermined threshold value or more, the control unit 380 may determine that the user authentication has succeeded.

Operations 1801 to 1811 are merely exemplary. There are various user authenticating methods based on ECG signals received through the plurality of electrodes, and the user authenticating methods may be implemented by various algorithms.

Figures 20, 21:
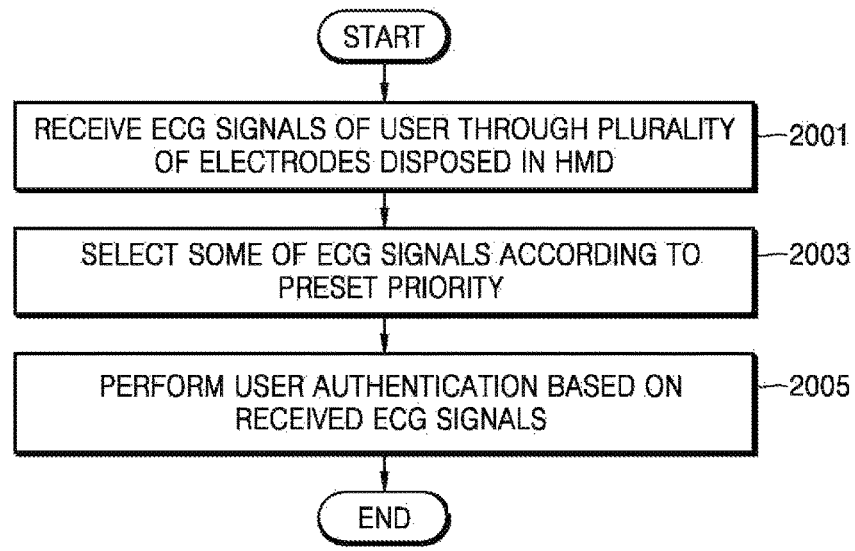
FIG. 20 is a flowchart of a user authenticating method using ECG, according to another exemplary embodiment.
FIG. 21 is a table for describing a user authenticating method using ECG, according to another exemplary embodiment.

FIG. 20 is a flowchart of a user authenticating method using ECG, according to another exemplary embodiment.

Referring to FIG. 20, in operation 2001, the control unit 380 may receive ECG signals from a user through a plurality of electrodes disposed in the HMD 100. When the user wears the HMD 100, ECG signals may be received from the user through a plurality of electrodes disposed in at least one of a contact portion of the HMD 100 contacting the user and a non-contact portion of the HMD 100 not contacting the user. For example, when the user wears the HMD 100, ECG signals may be received from the user through a plurality of electrodes disposed in at least one of the inner side of the temple middle portion 101-1 and the nose pad 104, which contact the user. In another example, when the user wears the HMD 100, ECG signals may be received from the user through a plurality of electrodes disposed in at least one of the outer side of the temple proximal end portion 101-2, the outer side of the temple distal end portion 101-3, and the upper side of the lens frame 103, which do not contact the user. For example, when the user touches (or contacts) the electrodes disposed in the left and right temple proximal end portions 101-2 with his or her hands, the control unit 380 may receive ECG signals from the user through the electrodes disposed in the left and right temple proximal end portions 101-2.

In operation 2003, the control unit 380 may select some of the plurality of ECG signals received in operation 2001 according to a preset priority.

An intensity (or magnitude), strength, or quality of the received ECG signal may be different according to portions where the plurality of electrodes contact the user while the user wears the HMD 100. For example, the intensity of the ECG signal received through the electrode disposed in the contact portion contacting the user may be weaker than the intensity of the ECG signal received through the electrode disposed in the non-contact portion. For example, the intensity of the ECG signal received through the electrode disposed in the inner side of the temple middle portion 101-1 contacting the user may be weaker than the intensity of the ECG signal received through the electrode disposed in the outer side of the temple proximal end portion 101-2 due to a user's hair or the like.

In another exemplary embodiment, even in the same configuration of the HMD 100, an intensity, strength, or quality of the received ECG signal may be different according to the position of the electrode. For example, when the temple 101 is contacted by the user's hand, the intensity of the signal received through the electrode disposed in the temple proximal end portion 101-2 may be stronger than the intensity of the signal received through the electrode disposed in the temple middle portion 101-1. In another example, when the temple 101 is contacted by the user's hand, the signal received through the electrode disposed in the temple proximal end portion 101-2 may be more accurate than the signal received through the electrode disposed in the temple middle portion 101-1. In other words, the ECG signal received through the electrode disposed in the temple proximal end portion 101-2 by the contact with the user's hand may have less noise than the ECG signal received through the electrode disposed in the temple middle portion 101-1 maintaining the contact with the user while the user wears the HMD 100.

In another exemplary embodiment, when the electrodes are disposed in a portion contacting the user while the user wears the HMD 100, an intensity (or magnitude), strength, or quality of the received ECG signal may be different according to portions of the electrodes. For example, the intensity of the ECG signal received through the electrode disposed in the nose pad 104 contacting the user may be stronger than the intensity of the ECG signal received through the electrode disposed in the inner side of the temple middle portion 101-1.

FIG. 21 is a table for describing a user authenticating method using ECG, according to another exemplary embodiment. In a case where a plurality of ECG signals are received through a plurality of electrodes, an example of selecting two ECG signals received through two electrodes is illustrated in FIG. 21.

Referring to FIG. 21, of the plurality of ECG signals received through the plurality of electrodes, ECG signals received through the electrodes disposed in the left and right temple proximal end portions 101-2 may be the most accurate signals. The ECG signals received through the electrodes disposed in the temple left/right proximal end portions 101-2 may have the highest SNR. For example, the signal received through the electrode disposed in the temple middle portion 101-1 or the temple distal end portion 101-3 may include much noise due to the user's hair or sweat. Two ECG signals received through one electrode disposed in the outer side of the temple proximal end portion 101-2 and another electrode disposed in the temple middle portion 101-1 may have the second highest SNR. Two ECG signals received through one electrode disposed in the outer side of the temple proximal end portion 101-2 and another electrode disposed in nose pad 104 may also have the second highest SNR. Two ECG signals received through two electrodes disposed in the left and right temple middle portions 101-1 may have the third highest SNR. A more accurate ECG signal may be received when spacing between electrodes is larger. For example, the ECG signals received through two electrodes disposed in the temple middle portions 101-1 may be less accurate than the ECG signals received through two electrodes disposed in the temple middle portion 101-1 and the temple proximal end portion 101-2. However, FIG. 21 is merely exemplary and the inventive concept is not limited thereto.

The control unit 380 may only use some ECG signals from among the plurality of ECG signals received through the plurality of electrodes for user authentication.

In another exemplary embodiment, the control unit 380 may use some of the unselected ECG signals from among the plurality of ECG signals received through the plurality of electrodes as auxiliary signals. For example, the control unit 380 may use some of the ECG signals, which are unselected from among the plurality of ECG signals received through the plurality of electrodes, to correct errors of the received ECG signals.

The control unit 380 may select some of the received ECG signals based on an SNR history of the ECG signals received through the plurality of electrodes. For example, as a result of ECG measurement for a predetermined time, when the SNR of the ECG signals received through the electrodes disposed in the left and right temple proximal end portions 101-2 and the nose pad 104 is higher than the SNR of the ECG signals received through the other electrodes, the control unit 380 may set priorities to be higher for a combination of electrodes disposed in the left and right temple proximal end portions 101-2 and the nose pad 104 and store the priorities. When the ECG signals are received through the plurality of electrodes, the control unit 380 may perform user authentication by using the ECG signals received using the high-priority electrodes disposed in the left and right temple proximal end portions 101-2 and the nose pad 104. In another exemplary embodiment, when the ECG signals are received through the plurality of electrodes, if an SNR of another combination of electrodes is measured to be higher than the set combination of electrodes, the control unit 380 may determine that an ECG signal of another user, not the first user of the HMD 100, is being received. When it is determined that the ECG signal of another user is received, the control unit 380 may set a threshold value for user authentication to a higher value.

In operation 2005, the control unit 380 may perform user authentication based on some selected ECG signals. Since operation 2005 is substantially the same as operation 1703 of FIG. 17, detailed descriptions thereof will be omitted.

Figure 22:
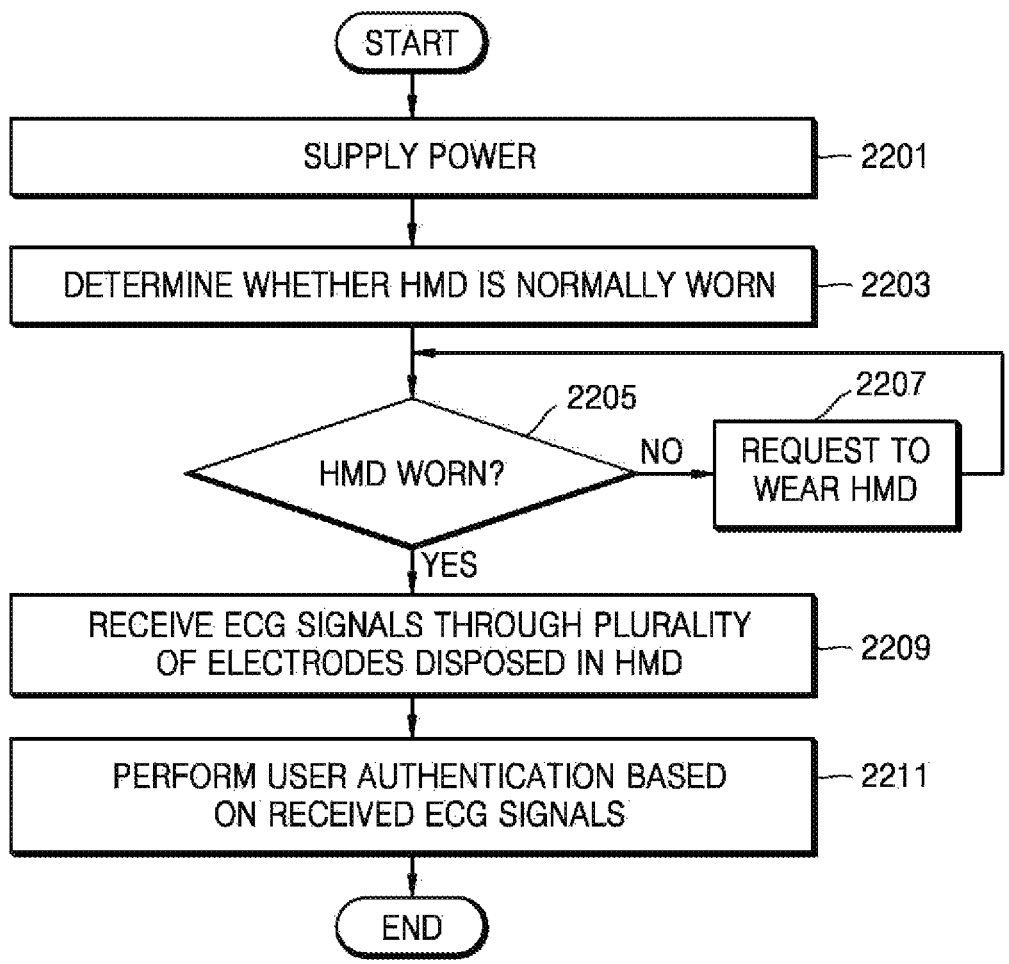
FIG. 22 is a flowchart of a user authenticating method using ECG, according to another exemplary embodiment.

FIG. 22 is a flowchart of a user authenticating method using ECG, according to another exemplary embodiment.

Referring to FIG. 22, in operation 2201, when a power button input is received from a user, power may be supplied to each element of the HMD 100.

In operation 2203, the control unit 380 may determine whether the user is wearing the HMD 100 correctly.

The control unit 380 may determine whether the user is wearing the HMD 100 correctly, according to whether ECG signals are received through a plurality of electrodes disposed in the HMD 100. For example, when the user wears the HMD 100 and the ECG signals are not received through the plurality of electrodes disposed in the HMD 100, the control unit 380 may determine that the user is not wearing the HMD 100.

In another exemplary embodiment, the control unit 380 may determine whether the user is wearing the HMD 100 correctly based on intensity (or magnitude), strength, or quality of the ECG signals received through the plurality of electrodes disposed in the HMD 100. For example, in a case where the user is not wearing the HMD 100 correctly, the intensity of the ECG signal received through a specific electrode may be weak, as compared with a case where the user wears the HMD 100 correctly. When the intensity of the ECG signal received through the specific electrode is low, the control unit 380 may determine that the user is not wearing the HMD 100 correctly.

The control unit 380 may determine whether the user is wearing the HMD 100 correctly based on an ECG signal received through electrodes contacting the user when the user wears the HMD 100. The control unit 380 may determine whether the user is wearing the HMD 100 correctly based on an ECG signal received through at least one of the electrodes 123 disposed on the inner side of the temple middle portion 101-1 and the electrode disposed in the nose pad 104, which contact the user when the user wears the HMD 100.

When the power is supplied in operation 2201, the control unit 380 may receive the ECG signal through the electrode disposed in the contact portion of the HMD 100 and may ignore the ECG signal received through the non-contact portion. For example, even though the user does not wear the HMD 100, the ECG signal may be received from the electrode attached to the lens frame 103 of the HMD 100 that is contactable with the user's hand. When the power is supplied, the control unit 380 may ignore the ECG signal received through the electrode attached to the upper side of the lens frame 103.

Figure 23:
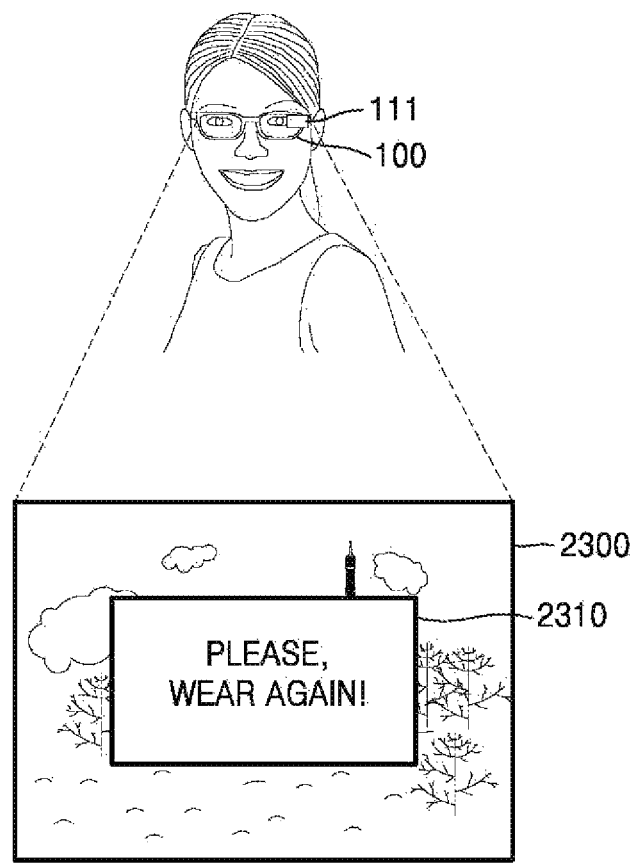
FIG. 23 is an exemplary diagram for describing a user authenticating method using an ECG, according to another exemplary embodiment.

In operation 2207, when it is determined in operation 2205 that the HMD 100 is not being worn correctly, the control unit 380 may output a request to wear the HMD 100 correctly or to adjust the HMD 100 as described with respect to FIG. 23. Operations 2209 and 2211 will be described after the description of FIG. 23.

FIG. 23 is an exemplary diagram for describing a user authenticating method using ECG, according to another exemplary embodiment.

As illustrated in FIG. 23, the control unit 380 may control the display unit 111 to display a message on the screen 2300 requesting the user to adjust the HMD 100 or to put it on again. For example, the control unit 380 may control the display unit 220 to output a window 2310 on which a message such as "Please adjust the HMD!" or "Please wear again!" may be displayed. In another example, the control unit 380 may control the audio output unit 325 to output words such as "Please adjust the HMD!" or "Please wear again!"

When the request to wear the HMD 100 correctly is made in operation 2207, the control unit 380 returns to operation 2203 to determine whether the HMD 100 is being worn correctly by the user.

In operation 2209, when it is determined in operation 2205 that the HMD 100 is being worn correctly, the control unit 380 may receive ECG signals through the plurality of electrodes disposed in the HMD 100. Since operation 2209 is substantially the same as operation 1701 of FIG. 17, detailed descriptions thereof will be omitted.

In some exemplary embodiment, operation 2209 may be omitted. For example, in operation 2203, when the ECG signals are received through the plurality of electrodes disposed in the HMD 100 so as to determine whether the HMD 100 is worn correctly, the control unit 380 may not receive ECG signals again through the plurality of electrodes disposed in the HMD 100. In another example, in operation 2203, when the ECG signals having intensity of the threshold value or more are received through the plurality of electrodes disposed in the HMD 100 so as to determine whether the HMD 100 is worn correctly, the control unit 380 may not receive ECG signals again through the plurality of electrodes disposed in the HMD 100.

In another exemplary embodiment, when it is determined in operation 2203 that the HMD 100 is worn correctly by receiving the ECG signals through the plurality of electrodes, the control unit 380 may receive ECG signals through other electrodes different from the plurality of electrodes used for determining whether the HMD 100 is worn correctly. For example, in operation 2209, when it is determined in operation 2203 that the HMD 100 is worn correctly based on the ECG signals received through the electrodes disposed in the contact portion (e.g., the inner side of the temple middle portion 101-1) of the HMD 100, the control unit 380 may not receive ECG signals through the electrodes disposed in the non-contact portion (e.g., the outer side of the temple proximal end portion 101-2) of the HMD 100. The control unit 380 may select the ECG signal having a stronger intensity by comparing the intensity of the ECG signal received in operation 2203 with the intensity of the ECG signal received in operation 2209. The control unit 380 may perform user authentication based on the ECG signal having the stronger intensity.

The control unit 380 may detect spreading of the temple 101 and set a user authentication rate for user authentication to a higher value. The user authentication rate may mean accuracy or reliability of the ECG signal acquired by ECG sensor 340-1 and image of the user's iris acquired by the imaging unit 362. For example, the control unit 380 may detect the spreading of the temple 101 based on information sensed by the acceleration sensor 342 or the like. When it is determined that the spreading degree of the temple 101 is a preset value or more, the control unit 380 may set the user authentication rate to be higher. A case where the spreading degree of the temple 101 is the preset value or more may be a case where other user wears the HMD 100.

In operation 2211, the control unit 380 may perform user authentication based on the received ECG signal.

Figure 24:
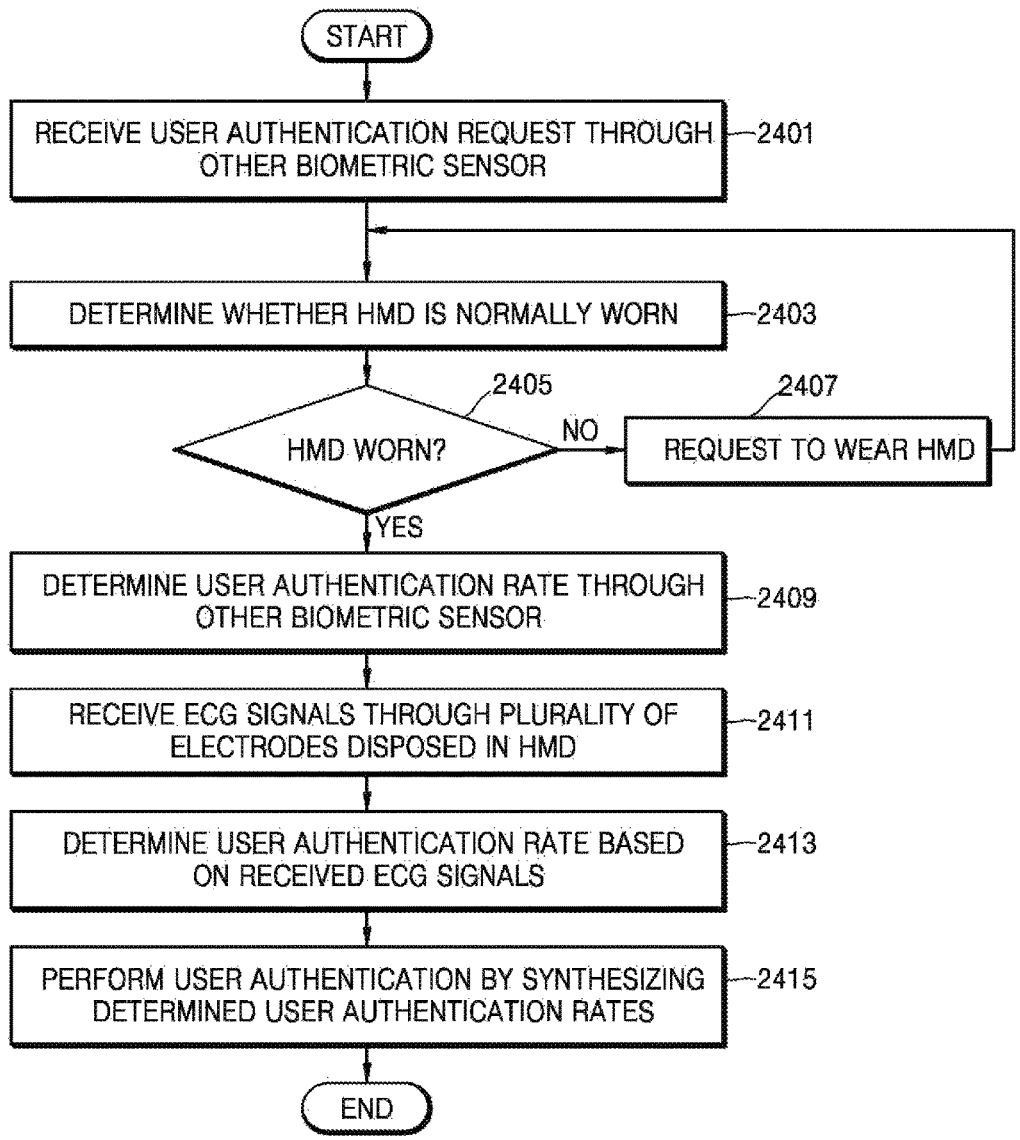
FIG. 24 is a flowchart of a user authenticating method using ECG, according to another exemplary embodiment.

FIG. 24 is an exemplary diagram for describing a user authenticating method using ECG, according to another exemplary embodiment.

Referring to FIG. 24, in operation 2401, the control unit 380 may receive a user authentication request through biometric sensors other than the ECG sensor 340-1.

Other biometric sensors may be, for example, the fingerprint sensor 340-4 and a pulse sensor (not shown). However, the inventive concept is not limited thereto. Any type of biometric sensors may be used as long as the biometric sensors are capable of sensing biometric information of the user and performing user authentication based on the sensed biometric information. For convenience of description, it is assumed that other biometric sensor is the fingerprint sensor 340-4, but the same may apply to other biometric sensors.

The user authentication request through the fingerprint sensor 340-4 may be a request for executing an application in which a fingerprint authentication is preset as an authenticating method. For example, in a case where the fingerprint authentication is required as the security setting to execute an application, when a user input of executing the application is received, the control unit 380 may confirm that the fingerprint authentication is set as the application authenticating method.

In operation 2403, the control unit 380 may determine whether the user is wearing the HMD 100 correctly. The control unit 380 may determine whether the user wears the HMD 100, according to whether ECG signals are received through the plurality of electrodes disposed in the HMD 100. In another exemplary embodiment, the control unit 380 may determine whether the user is wearing the HMD 100 correctly based on intensity (or magnitude), strength, or quality of the ECG signals received through the plurality of electrodes disposed in the HMD 100. The control unit 380 may determine whether the user is wearing the HMD 100 correctly based on an ECG signal received through an electrode contacting the user when the user is wearing the HMD 100.

In operation 2407, when it is determined in operation 2405 that the HMD 100 is not worn correctly, the control unit 380 may output a request to wear the HMD 100 correctly. When the request to wear the HMD 100 correctly is made in operation 2407, the control unit 380 returns to operation 2403 to determine whether the HMD 100 is now worn correctly by the user.

In operation 2409, when it is determined in operation 2405 that the HMD 100 is being worn correctly, the control unit 380 may receive biometric information from other biometric sensors and determine a user authentication rate based on the received biometric information.

When the biometric sensor is the fingerprint sensor 340-4, the control unit 380 may receive information about the user's fingerprint through the fingerprint sensor 340-4. The control unit 380 may extract a fingerprint feature from the received information about the user's fingerprint and compare the extracted fingerprint feature with a preregistered fingerprint feature. The control unit 380 may obtain a result of comparison between the extracted fingerprint feature and the preregistered fingerprint feature. The control unit 380 may determine a matching rate between the extracted fingerprint feature and the preregistered fingerprint feature based on the result of the comparison therebetween. The control unit 380 may determine the user authentication rate based on the matching rate between the extracted fingerprint feature and the preregistered fingerprint feature.

In operation 2411, the control unit 380 may receive ECG signals through the plurality of electrodes disposed in the HMD 100.

Operation 2409 and operation 2411 may be simultaneously performed. For example, in a case where the other biometric sensor is the fingerprint sensor 340-4, the information about the user's fingerprint and the ECG signals may be simultaneously received by one gesture of the user when the fingerprint sensor 340-4 is disposed to overlap one of the electrodes disposed in the HMD 100 or when at least one of the electrodes is adjacent to the fingerprint sensor 340-4. In another exemplary embodiment, the information about the user's fingerprint received from the fingerprint sensor 340-4 and the ECG signals received from the plurality of electrodes may be received at predetermined time intervals.

In some exemplary embodiments, operation 2411 may be omitted. For example, in operation 2403, when the ECG signals are received through the plurality of electrodes disposed in the HMD 100 so as to determine whether the HMD 100 is worn correctly, the control unit 380 may not receive ECG signals again through the plurality of electrodes disposed in the HMD 100. In another example, in operation 2403, when the ECG signals having intensity of the threshold value or more are received through the plurality of electrodes disposed in the HMD 100 so as to determine whether the HMD 100 is worn correctly, the control unit 380 may not receive ECG signals again through the plurality of electrodes disposed in the HMD 100.

In another exemplary embodiment, when it is determined in operation 2403 that the HMD 100 is worn correctly by receiving the ECG signals through the plurality of electrodes, the control unit 380 may receive ECG signals through other electrodes different from the plurality of electrodes used for determining whether the HMD 100 is worn correctly.

In operation 2413, the control unit 380 may determine the user authentication rate based on the received ECG signals.

For example, the control unit 380 may extract at least one feature point so as to calculate the pulse rate from the received ECG signals. The control unit 380 may calculate the pulse rate based on the extracted feature point. The control unit 380 may find an ECG signal, which is similar to the calculated pulse rate, from among a plurality of preregistered ECG signals. In order to match the found ECG signal with the feature point, the received ECG signal may be corrected. The control unit 380 may compare a waveform of the received ECG signal with a waveform of the found ECG signal. The control unit 380 may determine the matching rate between the waveform of the received ECG signal and the waveform of the found ECG signal based on the result of the comparison. The control unit 380 may determine the user authentication rate based on the matching rate between the waveform of the received ECG signal and the waveform of the found ECG signal.

In order to determine the user authentication rate based on the received ECG signal, the control unit 380 may set a weight value to the matching rate of at least some features of the waveform of the ECG signal. For example, in order to compare the waveform of the received ECG signal with the waveform of the found ECG signal, the control unit 380 may set the voltage of the R point, the length of the PR interval, the length of the QT interval, the length of the ST segment, and the length of the TP segment as a comparison reference. The control unit 380 may set weight values to a matching rate of the voltage of the R point, a matching rate of the length of the PR interval, a matching rate of the length of the QT interval, a matching rate of the length of the ST segment, and a matching rate of the length of the TP segment.

For example, the control unit 380 may set a weight value of 0.2 to the matching rate of the voltage of the R point, a weight of 0.4 to the matching rate of the length of the PR interval, a weight value of 0.1 to the matching rate of the length of the QT interval, a weight of 0.25 to the matching rate of the length of the ST segment, and a weight value of 0.05 to the matching rate of the length of the TP segment. The control unit 380 may determine the user authentication rate with respect to the ECG authentication by combing the matching rates for the features as at least one comparison reference of the waveform of the ECG signal and the weight values for the features as at least one comparison reference of the waveform of the ECG signal.

In operation 2415, the control unit 380 may perform user authentication by synthesizing the user authentication rate determined based on the biometric information received through other biometric sensors and the user authentication rate determined based on the ECG signals received through the plurality of electrodes disposed in the HMD 100. For example, the control unit 380 may sum the user authentication rate determined based on the biometric information received through other biometric sensors and the user authentication rate determined based on the ECG signals received through the plurality of electrodes disposed in the HMD 100 and determine that the user authentication has succeeded when the sum is a preset threshold value or more.

Figure 25:
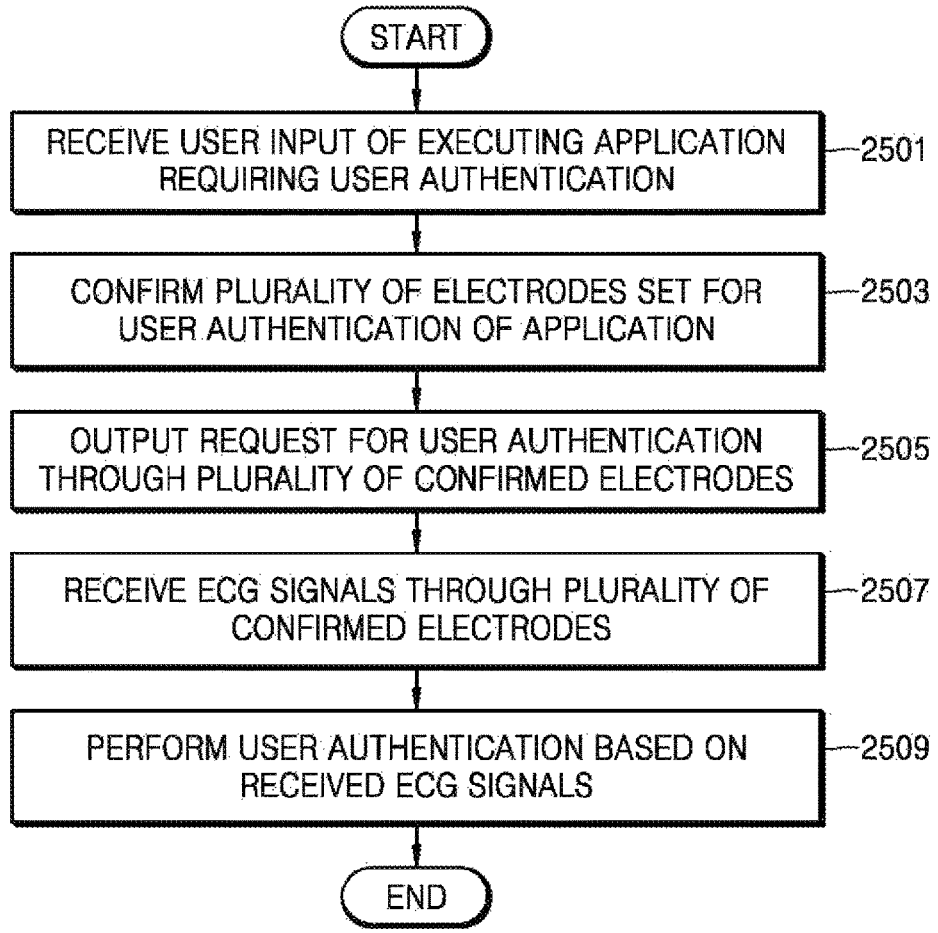
FIG. 25 is a flowchart of a user authenticating method using ECG, according to another exemplary embodiment.

FIG. 25 is a flowchart of a user authenticating method using ECG, according to another exemplary embodiment.

Referring to FIG. 25, in operation 2501, the control unit 380 may receive a user input of executing an application requiring user authentication. The user authentication set for executing the application may be user authentication based on the ECG signal. For example, when the user executes a payment application, the ECG authentication may be required to execute the payment application. When the request for the application execution is received, the control unit 380 may confirm that the ECG authentication is set for the application execution.

In operation 2503, the control unit 380 may confirm a plurality of preset electrodes with respect to the application requested to execute. A plurality of electrodes to be used for the user authentication based on the ECG signal may be set for each application. For example, in a case where the ECG signals are received from the plurality of electrodes disposed in the HMD 100, the control unit 380 may perform the user authentication of the payment application by using only the ECG signals received through the electrodes disposed in the outer sides of the left and right temple proximal end portions 101-2 among the plurality of electrodes. In another example, in order to output a security document for which security is set, the control unit 380 may use only the ECG signals received through the electrodes disposed in the nose pad 104 and the inner side of the temple middle portion 101-1 among the plurality of electrodes. The control unit 380 may set a plurality of electrodes to be used for the user authentication based on the ECG signal according to a security level required by the application, that is, an authentication level set for the application. For example, in order for accurate authentication of the payment application having a high authentication level, the control unit 380 may match the electrodes disposed in the outer side of the temple proximal end portion 101-2 with respect to the payment application so that the user authentication is performed based on the ECG signals having a stronger intensity, which are received through the electrodes disposed in the outer side of the temple proximal end portion 101-2 of the HMD 100.

In operation 2505, the control unit 380 may output a request for user authentication through the plurality of confirmed electrodes.

Operation 2507 will be described after the description of FIG. 26.

Figure 26:
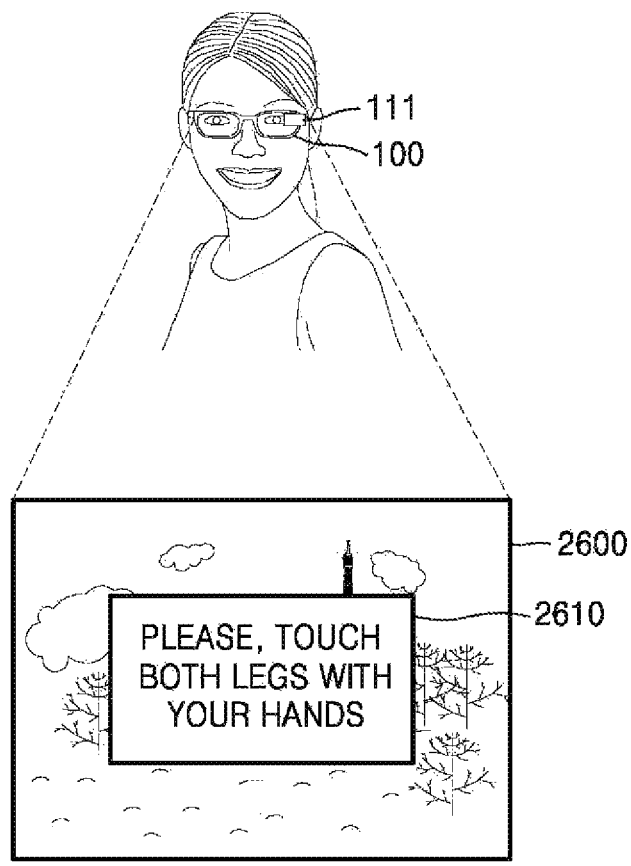
FIG. 26 is an exemplary diagram for describing a user authenticating method using an ECG, according to another exemplary embodiment.

FIG. 26 is an exemplary diagram for describing a user authenticating method using ECG, according to another exemplary embodiment.

As illustrated in FIG. 26, the control unit 380 may output a request for user authentication through the plurality of electrodes. For example, the control unit 380 may control the display unit 220 to output a window 2610 on which a message such as "Please touch both legs with your hands!" is displayed. In another example, the control unit 380 may control the audio output unit 325 to output a sound such as "Please touch both legs with your hands!".

In operation 2507, the control unit 380 may receive ECG signals through the plurality of confirmed electrodes. For example, the control unit 380 may receive ECG signals from the user through the plurality of electrodes set for the user authentication of the payment application, e.g., the plurality of electrodes disposed in the outer side of the temple proximal end portion 101-2 of the HMD 100.

In operation 2509, the control unit 380 may perform user authentication based on the received ECG signals. Since operation 2509 is substantially the same as operation 1703 of FIG. 17, detailed descriptions thereof will be omitted.

Figure 27:
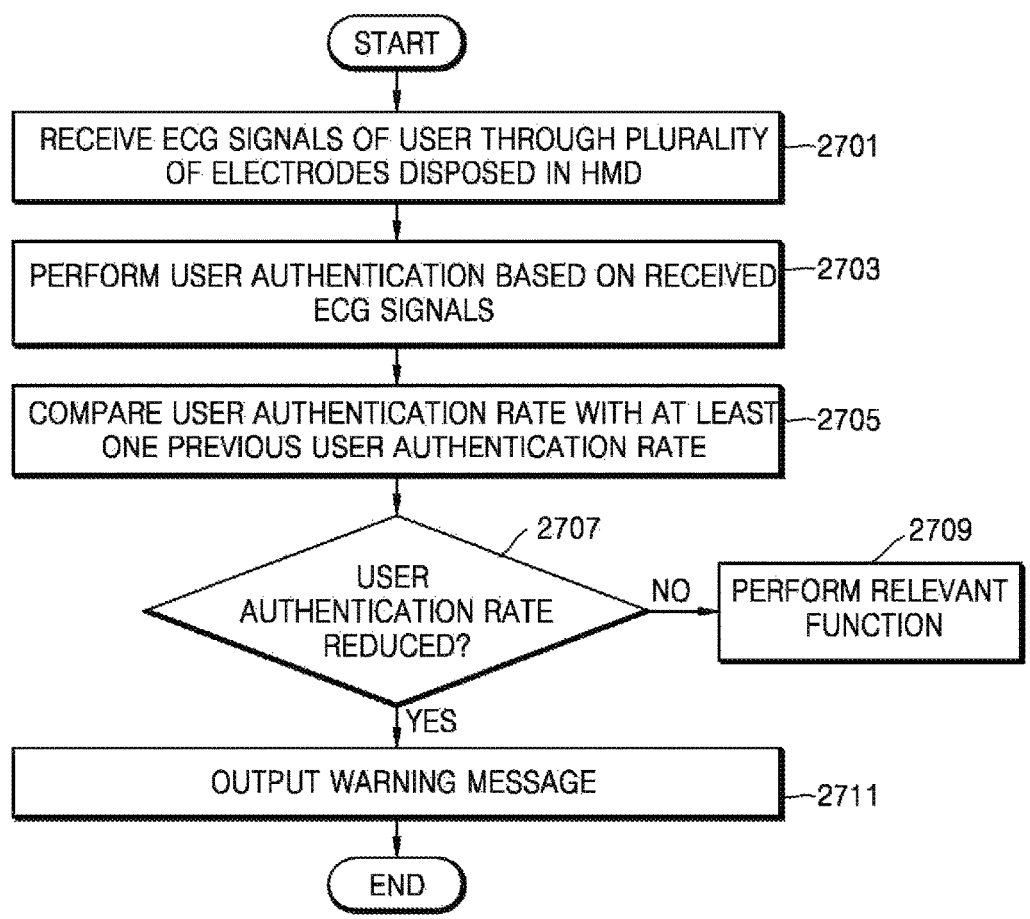
FIG. 27 is a flowchart of a user authenticating method using an ECG, according to another exemplary embodiment.

FIG. 27 is a flowchart of a user authenticating method using ECG, according to another exemplary embodiment.

Referring to FIG. 27, in operation 2701, the control unit 380 may receive ECG signals from a user through a plurality of electrodes disposed in the HMD 100. Since operation 2701 is substantially the same as operation 1701 of FIG. 17, detailed descriptions thereof will be omitted.

In operation 2703, the control unit 380 may perform user authentication based on the received ECG signals. For example, the control unit 380 may extract at least one feature point so as to calculate a pulse rate from the received ECG signals. The control unit 380 may calculate the pulse rate based on the extracted feature point. The control unit 380 may find an ECG signal, which is similar to the calculated pulse rate, from among a plurality of preregistered ECG signals. In order to match the found ECG signal with the feature point, the received ECG signal may be corrected. The control unit 380 may compare a waveform of the received ECG signal with a waveform of the found ECG signal. The control unit 380 may determine the matching rate between the waveform of the received ECG signal and the waveform of the found ECG signal based on the result of the comparison. When the matching rate between the waveform of the received ECG signal and the waveform of the preregistered ECG signal is a threshold value or more, the control unit 380 may determine that the user authentication has succeeded.

In operation 2705, the control unit 380 may compare the user authentication rate with at least one previous user authentication rate. For example, the control unit 380 may compare the matching rate of the ECG signal of the user authentication performed in operation 2703 with the matching rate of the user authentication performed before a predetermined time. The user authentication performed before the predetermined time may be user authentication performed for a predetermined period before the current user authentication. In another exemplary embodiment, the user authentication performed before the predetermined time may be user authentication performed at regular time intervals (or periodically). The control unit 380 may receive ECG signals, determine the matching rate of the user authentication based on the received ECG signals, and store the determined matching rate in the storage unit 390. When there is a user input or a preset period has arrived, the control unit 380 may compare the user authentication rate based on the currently received ECG signal with the user authentication rate determined based on the previously received ECG signal. For example, when it is determined that the user authentication rate based on the currently received ECG signal is reduced as compared with the user authentication rate determined based on the previously received ECG signal, the control unit 380 may determine that the user has heart problems.

When it is determined in operation 2707 that the user authentication rate based on the currently received ECG signal is not reduced as compared with the user authentication rate determined based on the previously received ECG signal, the control unit 380 may execute the relevant function in operation 2709.

For example, when the user authentication rate based on the currently received ECG signal is greater than the user authentication rate determined based on the previously received ECG signal, the control unit 380 may execute the function of the HMD 100 requiring the user authentication.

In operation 2711, when it is determined in operation 2707 that the user authentication rate based on the currently received ECG signal is reduced as compared with the user authentication rate determined based on the previously received ECG signal, the control unit 380 may output a warning message indicating that the user has heart problems.

Figure 28:
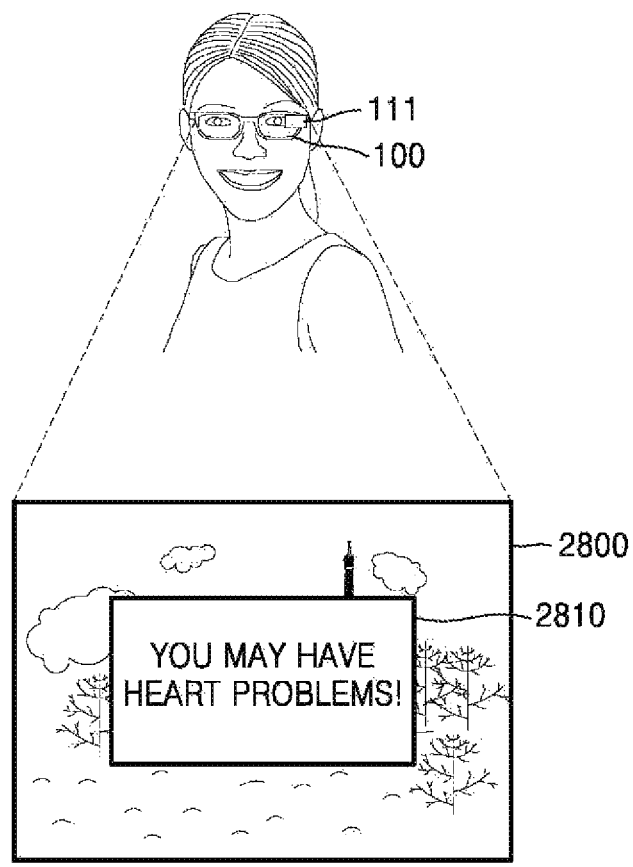
FIG. 28 is an exemplary diagram for describing a user authenticating method using an ECG, according to another exemplary embodiment.

FIG. 28 is an exemplary diagram for describing a user authenticating method using an ECG, according to another exemplary embodiment.

As illustrated in FIG. 28, the control unit 380 may control the display unit 315 to output a window 2810 on which a warning message such as "You may have heart problems!" is displayed. In another example, the control unit 380 may control the audio output unit 325 to output a sound such as "You may have heart problems!"

The user authenticating methods using the ECG and the HMDs 100 supporting the same, according to various exemplary embodiments, may support easy and convenient user authentication through the plurality of electrodes disposed on the HMD 100.

According to various exemplary embodiments, the user authenticating methods using biometric information and the HMDs supporting the same may perform the user authentication automatically without user knowledge.

The above-described exemplary embodiments may be embodied as computer programs and may be implemented by general-purpose digital computers that execute the computer programs by using a non-transitory computer-readable recording medium. In addition, the data structures used herein may be recorded in a non-transitory computer-readable recording medium through various manners. Examples of the computer-readable recording medium may include magnetic storage media (e.g., ROM, floppy disks, hard disks, etc.), optical readable media (e.g., CD-ROMs, or DVDs, etc.), and carrier waves (e.g., transmission via Internet, etc.).

While one or more exemplary embodiments have been described with reference to the figures, it will be understood by those of ordinary skill in the art that various changes in form and details may be made therein without departing from the spirit and scope as defined by the following claims.

What is claimed is:

1. A head mounted device (HMD) comprising:
    at least one camera configured to capture one or more partial region images of an iris;
    an electrocardiogram (ECG) sensor configured to receive ECG signals; and
    at least one processor configured to authenticate a user by acquiring at least one of the one or more partial region images, which are captured by the at least one camera, and the ECG signals, which are received through a plurality of electrodes,
    wherein the at least one processor is further configured to generate a normalized image to authenticate the user, by combining the one or more partial region images and by using a curvature of an inner contour line of the iris, which is included in the one or more partial region images.

2. The HMD of claim 1, wherein the at least one processor sets an authentication level for an application.

3. The HMD of claim 2, wherein the at least one processor is further configured to receive a user input to execute the application,
    wherein when the user input is received, the at least one processor authenticates the user by using one or both of the at least one partial region image and the ECG signals, which is set according to the authentication level.

4. The HMD of claim 3, wherein when one of the one or more partial region images and the ECG signals is not acquired, the at least one processor is configured to control at least one of the at least one camera and the ECG sensor so as to acquire an appropriate one of the one or more partial region images and the ECG signals.

5. A head mounted device (HMD) comprising:
    at least one camera configured to acquire one or more partial images of an iris of a user; and
    at least one processor configured to generate a normalized image for user authentication by combining the one or more partial images,
    wherein the at least one processor generates the normalized image by using a curvature of an inner contour line of the iris, which is included in the one or more partial images.

6. The HMD of claim 5, wherein the at least one processor generates the normalized image by using at least one of an outer contour line of the iris and an inner contour line of the iris, which are included in the one or more partial images.

7. The HMD of claim 5, wherein the at least one processor determines positions to be occupied in the normalized image by the one or more partial images and combines the one or more partial images based on the determined positions.

8. The HMD of claim 5, wherein the at least one camera is configured to capture an image of the iris of the user two or more times to generate the normalized image.

9. The HMD of claim 5, wherein, when the one or more partial images includes the inner contour line of the iris, the at least one processor estimates a size of a pupil from a radius of a virtual circle including the inner contour line by using the curvature of the inner contour line.

10. The HMD of claim 5, wherein, when the one or more partial images includes an outer contour line of the iris, the at least one processor estimates a size of the iris from a radius of a virtual circle including the outer contour line by using a curvature of the outer contour line.

11. The HMD of claim 5, further comprising a display configured to provide a user interface for capturing an image of the iris of the user, and configured to provide a user interface for guiding a position to be viewed by a user's eye so as to acquire partial images of specific parts the iris.

12. A head mounted device (HMD) comprising:
    a plurality of electrodes configured to detect ECG signals disposed in the HMD; and
    at least one processor configured to:

receive ECG signals through the plurality of electrodes,
measure a signal-to-noise ratio (SNR) of the received ECG signals,
compare the SNR of the received ECG signals to a threshold value,
perform user authentication based on the received ECG signals when the SNR of the received ECG signals is greater than or equal to the threshold value, and
perform the user authentication based on biometric information received from at least one biometric sensor when the SNR of the received ECG signals is less than the threshold value, wherein the at least one biometric sensor is different from an ECG sensor.

13. The HMD of claim 12, wherein the plurality of electrodes are disposed in at least one of a first contact portion that is disposed on an inner side of the HMD and contacts a user's head when the user wears the HMD, and a second contact portion that is contactable with other body parts except for the head.

14. The HMD of claim 12, wherein, when a plurality of ECG signals are received from the plurality of electrodes disposed in the HMD, the at least one processor determines at least one of the plurality of ECG signals for the user authentication according to a setting, and performs the user authentication based on the determined at least one ECG signal.

15. The HMD of claim 14, further comprising a display, wherein, when it is determined that the HMD is not worn by the user, the at least one processor controls the display to output guidance for wearing the HMD.

16. The HMD of claim 12, wherein the at least one processor determines whether the HMD is worn by the user.

17. The HMD of claim 12, wherein the at least one processor is configured to:

receive a user input for the user authentication through the at least one biometric sensor,
receive the biometric information of the user through the at least one biometric sensor,
determine a first matching rate between the received biometric information of the user and preregistered biometric information corresponding to the biometric information,
determine a second matching rate between the ECG signals received through the plurality of electrodes and the preregistered ECG signal, and
perform the user authentication by combining the first matching rate and the second matching rate.

18. The HMD of claim 12, wherein the at least one processor is further configured to:

receive a user input to execute an application,
confirm electrodes set for the user authentication for the application, for which the user input is received, among the plurality of electrodes, and
receive ECG signals through the confirmed electrodes.

19. The HMD of claim 12, further comprising a display, wherein the at least one processor is configured to:

determine a third matching rate between the ECG signals received through the plurality of electrodes and a preregistered ECG signal,
compare the third matching rate with at least one fourth matching rate determined based on at least one ECG signal received for a predetermined time before the reception of the ECG signals, and
control the display to output a message indicating that the user has health problems when the third matching rate is less than the at least one fourth matching rate.

* * * * *